United States Patent [19]

Livak et al.

[11] Patent Number: 5,102,785
[45] Date of Patent: Apr. 7, 1992

[54] METHOD OF GENE MAPPING

[75] Inventors: Kenneth J. Livak, Wilmington, Del.; Sydney Brenner, Cambridge, England

[73] Assignee: E. I. Du Pont de Nemours and Company, Wilmington, Del.

[21] Appl. No.: 185,741

[22] Filed: Apr. 25, 1988

Related U.S. Application Data

[63] Continuation-in-part of Ser. No. 103,105, Sep. 28, 1987, abandoned.

[51] Int. Cl.$^5$ .................... C12Q 1/68; G01N 33/48; G01N 33/566; C07H 15/12
[52] U.S. Cl. ........................................ 435/6; 435/91; 536/26; 536/27; 536/28; 536/29; 436/94; 436/501; 935/77
[58] Field of Search ..................... 435/6.91, 5; 436/94, 436/501, 63; 935/77, 78; 536/26, 27, 28, 29

[56] References Cited

U.S. PATENT DOCUMENTS

| | | | |
|---|---|---|---|
| 4,661,408 | 4/1987 | Lau et al. | 530/413 |
| 4,672,040 | 6/1987 | Josephson | 435/6 |
| 4,849,077 | 7/1989 | Rosenthal et al. | 435/6 |
| 4,851,331 | 7/1989 | Vary et al. | 435/6 |
| 4,855,225 | 8/1989 | Fung et al. | 435/6 |
| 4,882,127 | 11/1989 | Rosenthal et al. | 435/301 |

FOREIGN PATENT DOCUMENTS

0278453 11/1986 Japan .................... 435/91

OTHER PUBLICATIONS

Genome Mapping and Sequencing, 4/27-5/1, 1988, Cantor et al., The Genome of Caenorhabditis by Coulson et al.
DNA Fingerprinting by Sampled Sequencing, Brenner et al., PNAS (USA) 86:8902-8906, 1989.
Figure 3-1, Mapping different levels of radiation (Unpublished).
Unidentified paper, discusses various fingerprinting techniques.
DNA Fingerprinting by Sampled Sequencing by McGuigan et al., The Du Pont Merck Pharmaceutical Company (unpublished).
Prober, J. M. et al., Science 238:336-341 (1987).
Chem. Abstr. 112:94991e (1990).
Ansorge et al., Nuc. Acids Res. 15(11):4593-4602 (1987).
Olson et al., Proc. Natl. Acad. Sci., U.S.A., 83:7826-7830 (1986).
Coulson et al., Proc. Natl. Acad. Sci., U.S.A., 83:7821-7825 (1986).

Primary Examiner—Robert A. Wax
Assistant Examiner—Stephanie W. Zitomer

[57] ABSTRACT

The method described characterizes each DNA segment to be mapped by cleaving it to produce DNA fragments which are then end labeled with a reporter(s) specific to the end nucleotides of each fragment. The labeled fragments are again cleaved to produce short fragments which are separated according to size. The short fragments are analyzed as to report identify and size which is indicative of the character of each fragment. By derivatizing the cleaved ends of the primary cleaved fragments, the labeling may be delayed until the second cleavage. Prior to the labeling the derivatized fragments, all underivatized fragments are removed, the derivatized fragments being immobilized.

39 Claims, 2 Drawing Sheets

METHOD OF GENE MAPPING

CROSS REFERENCE TO RELATED APPLICATION

This application is a continuation-in-part of an application Ser. No. 103,105, filed Sept. 28, 1987 entitled "Method of Gene Mapping" by Kenneth James Livak and Sydney Brenner, now abandoned.

FIELD OF THE INVENTION

This invention relates to a method for relating DNA segments to each other by comparing a limited number of polynucleotide fragments which make up each segment.

BACKGROUND OF THE INVENTION

It often is desirable in molecular biology to determine the relatedness of DNA segments. Such determinations at the nucleotide sequence level have many uses in the detection and molecular analysis of DNAs from different organisms and in the construction of physical and genetic maps. The most precise method for comparing segments of DNA is to determine the entire nucleotide sequence of each segment. For large DNA segments, sequencing becomes prohibitively time-consuming and expensive. Thus, at the present time, it is not practical to use extensive sequencing to compare DNA segments when the segments are large or when a large number of segments are being compared.

Restriction enzymes provide a tool to rapidly analyze DNA segments to obtain a limited amount of sequence information. Each restriction enzyme recognizes a specific sequence of DNA, normally four to eight nucleotide pairs in length, and cleaves DNA at or near this recognition sequence. Digestion of a DNA segment with a particular restriction enzyme thus generates a characteristic array of fragments. Typically, these fragments are separated according to length by electrophoresis through an appropriate gel matrix. The sizes of the fragments are dependent on the exact sequence recognized by the restriction enzyme and the spatial distribution of the recognition sequence within the DNA segment. Thus, cleavage of a DNA segment with a restriction enzyme indicates that a particular short recognition sequence is present; the number of fragments produced indicates how many times the recognition sequence occurs; and the sizes of the fragments indicate the distance, in nucleotides, between adjacent recognition sites.

The relatively simple steps involved in digesting DNA with restriction enzymes and in electrophoresing DNA fragments have made restriction-fragment analysis a routine method for characterizing and comparing DNA segments. If two segments of DNA have restriction fragments of the same length, then there is an increased likelihood that the segments are similar in sequence or overlapping. The greater the number of restriction fragments in common, the higher the probability that any two DNA segments are related. Two procedures have been described that demonstrate the utility of using restriction-fragment comparisons to determine the relatedness of a large number (5000-10,000) of DNA segments. These two procedures are the global mapping method described by Olson et al. [Proc. Natl. Acad. Sci. U.S.A. 83:7826-7830 (1986)] and the fingerprint mapping method described by Coulson et al. [Proc. Natl. Acad. Sci. U.S.A. 83:7821-7825 (1986)].

The first step in the global mapping method is to digest each DNA segment with a restriction enzyme or combination of restriction enzymes to generate a collection of restriction fragments. (In the example presented by Olson et al., each DNA segment was digested with a combination of HindIII and EcoRI to generate fragments with an average size of 1200 bp.) Each restriction digest is electrophoresed in a separate lane through an agarose gel in order to separate fragments according to length. The DNA restriction fragments are visualized by staining each gel with ethidium bromide and photographing the gel using ultra violet illumination. The size of each restriction fragment is determined by comparing its electrophoretic mobility with the mobilities of known size standards that were electrophoresed in a parallel lane of each gel. Thus, each DNA segment is characterized by a list of restriction fragment sizes. A data base is constructed that contains fragment-size lists for all the DNA segments being compared. With the aid of a computer program, the fragment-size lists are compared in a pairwise manner in order to determine the number of fragments of common size. DNA segments with a significant number of overlaps are considered to be related. In this manner related DNA segments spanning regions greater than 100,000 bp can be identified.

The Olson et al. procedure is referred to as a global mapping method because almost all the fragments produced in the restriction digest are used in the construction of the fragment-size lists. The inclusion of nearly all fragments requires the use of a separation method that can resolve fairly large fragments, such as electrophoresis through an agarose gel. Although the use of an agarose gel allows analysis of large fragments, the ability to discriminate and accurately size closely-spaced fragments on an agarose gel is somewhat limited. This problem is addressed in the fingerprint mapping method of Coulson et al. by reducing the size of the fragments being analyzed to approximately 1000 nucleotides or smaller. Fragments of this size can be resolved with single base resolution on a denaturing acrylamide gel.

In the fingerprint mapping method of Coulson et al., each DNA segment is first cleaved with a restriction enzyme that leaves a 5' overhang. The ends of these fragments are labeled by incubation with a DNA polymerase in the presence of a radioactive nucleotide. These radioactively-labeled fragments are then digested with a second restriction enzyme that cleaves quite frequently to generate fragments that are now fairly short in length (average size approximately 200 bp). Each collection of DNA fragments is then separated according to length by electrophoresis through a denaturing polyacrylamide gel. Although each sample may contain a large number of different fragments, only those fragments that have an end generated by cleavage with the first restriction enzyme are radioactively labeled. The locations of these labeled fragments on the gel are detected by autoradiography. The sizes of the detected fragments are determined by comparison to the mobilities of known size standards. As in the global mapping method, fragment-size lists are compared in order to determine which DNA segments are related. Coulson et al. were able to identify clusters of related DNA segments that spanned regions 35,000 to 350,000 bp in size.

The global mapping method, the fingerprint mapping method, and other similar methods use a fragment-size list to characterize the identity of each DNA segment being examined. Each fragment in the fragment-size list represents one bit of information that can be used in comparing the relatedness of DNA segments. One disadvantage of these methods is that the amount of information about each DNA segment is limited to the number of fragments in the fragment-size list. If the fragments could be differentiated in some other way besides just size, more information would be available for making comparisons. Increasing the information content of each fragment in the fragment-size list provides better discrimination in deciding which overlaps between DNA segments are significant.

Another disadvantage of both the global and fingerprint mapping methods is that a number of steps are required after electrophoresis in order to obtain digital information that can be used in making comparisons. In the global mapping method gels must be stained with ethidium bromide and photographed in order to record the location of each DNA fragment in the gel. In the fingerprint mapping method gels must be exposed to X-ray film and the X-ray film must be developed in order to obtain a record of the mobility of each DNA fragment. In both cases the photographs or autoradiograms must be analyzed in order to digitize the mobility information. These manual manipulations increase the time and effort required to perform the mapping procedures.

SUMMARY OF THE INVENTION

Many of the problems associated with the prior mapping methods are overcome by the methods of this invention. A method is described for rapidly characterizing and mapping DNA segments according to a modification of the Coulson et al. fingerprint mapping method where restriction fragments are differentially labeled by attachment of nucleotide-specific reporter molecules. The advantage of differential labeling is that it eliminates the reliance on fragment size as the sole criterior for rapidly classifying restriction fragments. Differential labeling is achieved by first cleaving a DNA segment made up of duplex strands of nucelotides with a first restriction enzyme or enzymes to produce fragments with an overhang of nucleotides at the cleaved ends. Although it may be an exact end restriction enzyme, preferably, the restriction enzyme is one of a group of ambiguous-end restriction enzymes that generate DNA molecules with a 5' overhang strand and a 3' recessed strand. Next, a reporter specific for each nucleotide in each overhang is attached to the 3' recessed strand of the fragment ends. Following cleavage of the fragments with a second restriction enzyme to produce short DNA fragments, the short fragments are separated according to size and analyzed for the presence of reporters. Thus, each labeled short fragment is characterized not only by its size, but also by the type of reporter attached.

Alternatively, the primary restriction enzyme or enzymes may be from a group of restriction enzymes that generate DNA molecules with a 3' overhang strand (and a 5' recessed strand) or from a group of restriction enzymes which generate DNA molecules with blunt ends. Although exact end restriction enzymes may be used, in each case the use of ambiguous-end restriction enzymes is preferred. In order to label 3' overhangs and blunt ends, use is made of the 3' exonuclease activity inherent in some DNA polymerases to remove 3' nucleotides at each cleaved end, thus converting each 3' overhang or blunt end into a 5' overhang. As part of the same reaction, the DNA polymerase attaches to each 3' end a reporter complementary to each nucleotide in the newly created 5' overhang. Thus, 5', 3' and blunt end restriction enzymes, either ambiguous or exact end, may be used in the gene mapping methods of this invention.

The use of the nucleotide-specific reporters allows the nucleotide sequence at the labeled end of each restriction fragment to be determined. This terminal sequence provides another criterion for comparing DNA fragments other than size. Also, knowledge of each terminal sequence is advantageous because it provides information about the order of restriction fragments within the parent DNA segment. Cleavage of DNA with an ambiguous-end restriction enzyme produces ends with overhangs of complementary sequence. Thus, if two fragments have a complementary terminal sequence, they are likely adjacent; and, conversely, if two fragments do not have complementary terminal sequences, they cannot be adjacent. This rudimentary order information is useful in comparing the relatedness of different DNA segments and in mapping the location of restriction sites in a single DNA segment.

A DNA sequencer using suitable nucleotide reporters, preferably the DNA sequencer Genesis 2000 TM sold by E. I. du Pont de Nemours and Company, Wilmington, Del. 19898, an instrument capable of detecting DNA fragments having fluorescent reporters, makes it possible readily to add sequence information to the size information being compared in the fingerprint mapping method. The use of the labeled dideoxynucleotides in this invention takes advantage of certain restriction enzymes that cleave DNA leaving ends or overhangs containing bases which are not included in the restriction enzyme recognition specificity.

In an alternative method of this invention, the versatility of the above described methods are greatly enhanced by attaching the nucleotide specific reporters to the secondary cleaved end after the second cleavage. This permits virtually any restriction enzyme to be used for the primary cleavage. Also by attaching the reporter after the second cleavage, larger DNA molecules (typically those 50 kilobases and larger) may be readily mapped. The problem occurring with large DNA molecules is that it is necessary to separate the subset of labeled fragments from the remainder of the DNA to prevent distortion of the DNA fragment pattern caused by overloading the size fractionating gel.

According to this alternative method, specific binding substances (e.g., one member a ligand and the other member a receptor) or pairs are used. One member (the ligand) is attached to the cleaved ends of the primary cleavage fragments. These ends will be referred to hereinafter in this discussion as the "anchor ends". Next the DNA fragments are cleaved a second time using a different restriction enzyme to provide shorter fragments. The shorter fragments with an anchor end are separated from the remainder of DNA fragments. This may be accomplished by the use of a solid support coated with or secured on the outside with the other member (receptor). The shorter fragment anchor ends bind to the other member of the binding pair on the solid support. So bound, the solid support is separated from the unbound DNA fragments and reporter labeled nucleotide(s) are attached to the free end of each of the separated shorter fragments. The labeled shorter fragments are removed from the solid support and fractionated. Each fragment size and reporter identity are recorded for use in the mapping procedure.

The end result of these procedures is to characterize a DNA segment with a list of fragments where each fragment is identified by both its size and its 3' terminal bases. Fragment lists of different DNA segments can be compared, searching for fragments that are identical in size and terminal base identity. A significant number of matching fragments indicates that two DNA segments are related. Inclusion of the 3' terminal base(s) identity adds significantly to the amount of information in each fragment list. This means that comparisons of DNA segments can be accomplished more rapidly and accurately than with lists that rely solely on fragment size. Thus, if fragments from large genomes are being compared, the methods of this invention considerably enhances the confidence with which overlaps can be determined.

DESCRIPTION OF THE DRAWINGS

The present invention will be better understood by considering the Examples in connection with the accompanying drawings in which.

DETAILED DESCRIPTION OF THE PREFERRED METHODS

Figure 1:
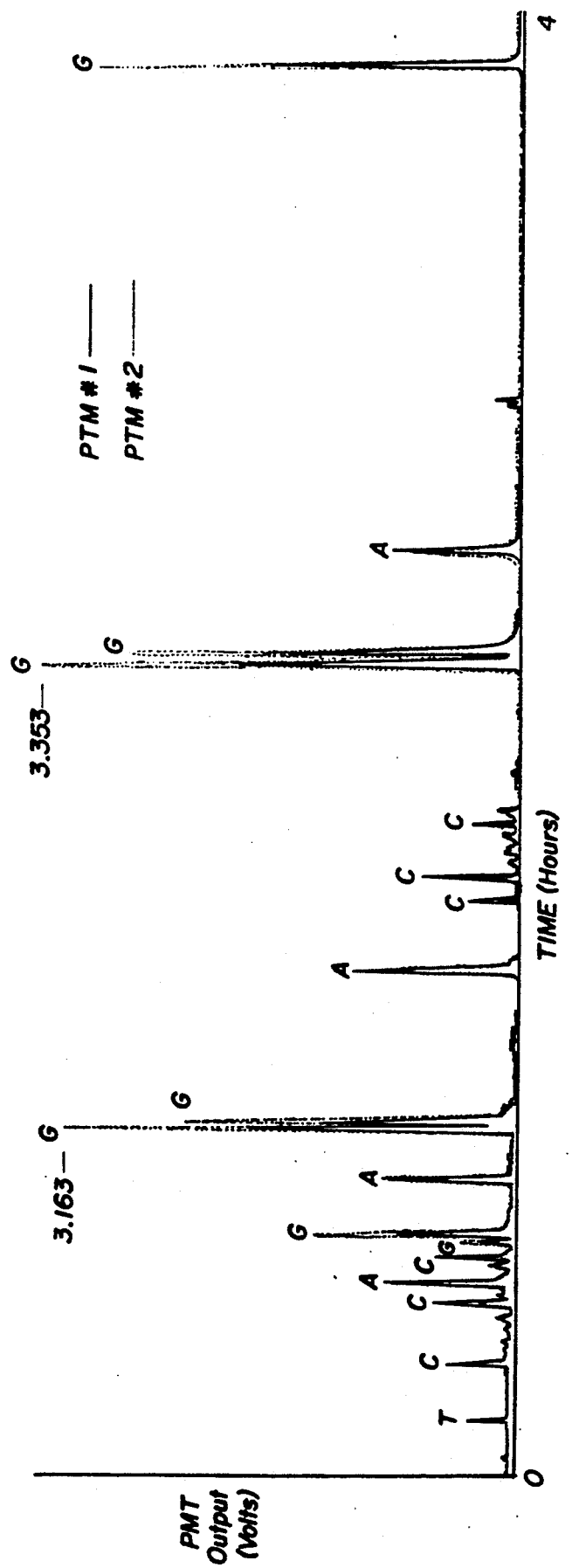
FIG. 1 is a plot of photomultiplier tube output as the ordinant and time as the abscissa depicting fluorescently labeled DNA fragments from the Becker strain of pseudorabies virus.

The method of this invention involves mapping DNA in a manner which provides information not only as to the size of DNA fragments but also information as to which nucleotides are on the ends of each fragment. It provides a means to rapidly characterize DNA segments by attaching distinguishable nucleotide-specific reporters to restriction fragment ends. These characterizations can be used to compare different DNA segments for relatedness and to help determine restriction maps, that is, the spatial distribution of restriction sites along a DNA segment.

To implement the method, restriction enzymes are used to cleave the phosphodiester backbone in each strand of double-stranded DNA. Depending on the particular restriction enzyme, this cleavage results in a pair of complementary cleaved ends in which, for each cleaved end, one strand of DNA has a 5' overhang and the other DNA strand has a 3' recess (also it can result in a blunt end, or a 3' overhang). An example of a 5' overhang is shown by the structure:

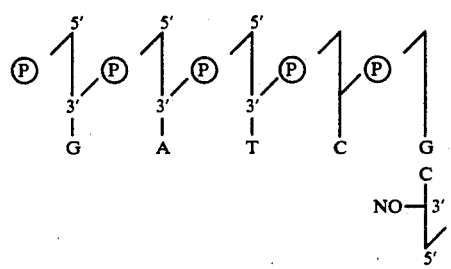

The number and identity of the nucleotides in the 5' overhang depends on the particular restriction enzyme.

For the restriction enzymes discovered so far, the number of nucleotides in the 5' overhang ranges from one to five.

The 5' overhangs of one DNA strand generated by many restriction enzymes are suitable substrates for DNA polymerases. In the presence of the four natural deoxyribonucleoside triphosphates (dNTP's), a DNA polymerase will repeatedly attach nucleotides to the recessed 3' hydroxyl group of the other strand until it fills in the length of the 5' overhang, resulting in a blunt-ended fragment. The nucleotides added to the 3' recessed end are complementary to the nucleotides in the 5' overhang. If one or all the dNTP's are replaced with reporter-containing analogues, then a DNA polymerase will attach these reporters to the free 3' hydroxyl group, resulting in an end-labeled restriction fragment. If the reporters are nucleotide-specific, then restriction fragments can be differentially labeled with reporters complementary to the nucleotides in the 5' overhang.

The restriction enzymes that generate 5' overhangs can be grouped into two subclasses. For the first type of enzyme, the nucleotides in the 5' overhang are exactly defined. These will be referred to as 5'-exact-end restriction enzymes. For the second type of enzyme, the 5' overhang can contain several possible nucleotide combinations. These will be referred to as 5'-indeterminate-end or 5'-ambiguous-end restriction enzymes. In order to achieve nucleotide-specific differential labeling of restriction fragments, the preferred approach is to use 5'-ambiguous-end restriction enzymes. Below is a list of known 5'-ambiguous-end restriction enzymes that could be used in this application and the ends generated by cleavage with each enzyme. N denotes that any base (A,C,G, or T) can be present. In some cases, more than one enzyme will produce the same type of end. These are known as isoschizomers. Only one member of each isoschizomer family is listed.

| AccI | —GT<br>—CAKM | MKAC—<br>TG— | M = A or C<br>K = G or T |
|---|---|---|---|
| AflIII | —A<br>—TGYRC | CRYGT—<br>A— | R = A or G |
| AvaI | —C<br>—GRGCY | YCGRC—<br>G— | Y = C or T<br>R = A or G |
| AvaII | —G<br>—CCWG | GWCC—<br>G— | W = A or T |
| BanI | —G<br>—CCRYG | GYRCC—<br>G— | Y = C or T<br>R = A or G |
| BbvI | —GCAGCNNNNNNNN<br>—CGTCGNNNNNNNNNNNN | NNNNNNNN—<br>NNNN— | |
| BinI | —GGATCNNNN<br>—CCTAGNNNN | NNNNNNNN—<br>NNNNNNN— | |
| BspMI | —ACCTGCNNNN<br>—TGGACGNNNNNNNN | NNNNNNNN—<br>NNNN— | |
| BstEII | —G<br>—CCANTGG | GTNACC—<br>G— | |
| BstNI | —CC<br>—GGW | WGG—<br>CC— | W = A or T |
| DdeI | —C<br>—GANT | TNAG—<br>C— | |

| | | | |
|---|---|---|---|
| Eco0109 | —RG<br>—YCCNG | GNCCY—<br>GR— | R = A or G<br>Y = C or T |
| EcoRII | —N<br>—NGGWCC | CCWGGN—<br>N— | W = A or T |
| Fnu4HI | —GC<br>—CGN | NGC—<br>CG— | |
| FokI | —GGATGNNNNNNNNN<br>—CCTACNNNNNNNNNNNNN | NNNNNNNN—<br>NNNN— | |
| HgaI | —GACGCNNNNN<br>—CTGCGNNNNNNNNN | NNNNNNNN—<br>NNN— | |
| HinfI | —G<br>—CTNA | ANTC—<br>G— | |
| MaeIII | —N<br>—NCANTG | GTNACN—<br>N— | |
| MstII | —CC<br>—GGANT | TNAGG—<br>CC— | |
| NciI | —CC<br>—GGS | SGG—<br>CC— | S = G or C |
| PpuMI | —RG<br>—YCCWG | GWCCY—<br>GR— | R = A or G,<br>Y = C or T<br>W = A or T |
| RsrII | —CG<br>—GCCWG | GWCCG—<br>GC— | W = A or T |
| Sau96I | —G<br>—CCNG | GNCC—<br>G— | |
| ScrFI | —CC<br>—GGN | NGG—<br>CC— | |
| SfaNI | —GCATCNNNNN<br>—CGTAGNNNNNNNNN | NNNNNNNN—<br>NNNN— | |
| StyI | —C<br>—GGWWC | CWWGG—<br>C— | W = A or T |
| TthIIII | —GACN<br>—CTGNN | NNGTC—<br>NCAG— | |

The labeled restriction fragments are digested a second time with a different restriction enzyme to generate still shorter fragments. The shorter fragments are then size separated, typically by gel electrophoresis, and the reporters on the separated fragments detected. This provides both size and nucleotide sequence information for each separated fragment which greatly facilitate mapping and comparison of fragments for similarities as described.

By way of illustration, the execution of this method, using preferred fluorescent reporters for the application of an enzyme leaving restriction fragments with a 5' overhang, requires four steps.

Step 1-DNA segments are cleaved to generate restriction fragments with 5' overhangs by incubating each DNA sample under the appropriate conditions with a restriction enzyme or combination of restriction enzymes, preferably one or more of the 5'-ambiguous-end restriction enzymes. (At this point, the restriction fragments may be purified by ethanol precipitation or some other means, but this is generally not necessary.)

Step 2-Nucleotides with nucleotide specific reporters, complementary to the nucleotide or nucleotides in each 5' overhang, are attached to the recessed 3' ends of the restriction fragments. While any reporters can be used, such as those sold by Applied Biosystems, Inc., Foster City, Calif., fluorescent reporters of the type sold for use in the Du Pont Genesis ™ DNA sequencer are preferred. These reporters have similar stabilities and do not affect the electrophoretic separation characteristic of the nucleotides they are attached to. The preferred reporters are one of a set of chain terminators, more specifically the flourescence-labeled 2',3'-dideoxynucleoside triphosphates (F-ddNTP's):
7-(SF505-Sar-AP3)ddc7GTP [15],
7-(SF512-Sar-AP3)ddc7ATP [14],
5-(SF519-Sar-AP3)ddCTP [13], and
5-(SF526-Sar-AP3)ddTTP [12].

(The compound numbers refer to the structures shown below)

The preferred method for attaching reporters is to incubate the collection of restriction fragments under the appropriate conditions with a DNA polymerase and a mixture of F-ddNTP's and unlabeled dNTP's. At each 3' restriction fragment end, this incubation results in the attachment of a distinctive fluorescence-labeled dideoxynucleotide complementary to each nucleotide in the 5' overhang. The selection of DNA polymerase depends upon the reporter substrate being attached. For the F-ddNTP's, reverse transcriptase and phage T7 DNA polymerase are appropriate DNA polymerases. The relative concentrations of F-ddNTP's and unlabeled dNTP's depends upon the number of reporters to be attached to each restriction fragment end.

If it is desired to attach only one reporter per end, then only F-ddNTP's are included in the incubation. If the 5' overhangs consist of more than one nucleotide and it is desired to attach more than one reporter at the 3' recessed strand end of each, then unlabeled dNTP's are also included. At each possible addition point on the recessed strand, either a F-ddNTP is added and the chain is terminated and labeled, or a dNTP is added and the chain is now a substrate for further addition. The F-ddNTP and dNTP concentrations are adjusted to give a suitable distribution of labeled fragments, differing in length by one nucleotide. After the labeling incubation, the DNA polymerase is inactivated by incubation at elevated temperature or some other means. (The labeled fragments can be purified by ethanol precipitation or some other means).

Step 3-The labeled fragments are next digested with a second restriction enzyme or combination of restriction enzymes in order to generate shorter fragments. Any restriction enzymes can be used at this point as long as they are different than the restriction enzymes used in the primary cleavage. This secondary cleavage serves two purposes. First, after the labeling reaction, both ends of each DNA fragment are labeled and this double-labeling would interfere with effective discrimination of the nucleotide-specific reporters. Thus, it is desirable to use a secondary cleavage to generate shorter fragments so that, in general, each labeled end is on a separate fragment of distinct size. Second, the generation of shorter fragments allows the use of separation procedures that can achieve single-base resolution, such as electrophoresis through denaturing polyacrylamide gels. (Again, the DNA fragments can be purified by ethanol precipitation or some other means.)

Step 4-The DNA fragments present after the secondary cleavage reaction are separated according to size and analyzed for the presence and identity of nucleotide-specific reporters. The preferred method is to use the Du Pont Genesis 2000 ™ gel electrophoresis and detection system. Other fluorescence detector and nucleotide-specific reporters may be used as desired. The reporters need not be fluorescent. With the Du Pont system, the time it takes for a labeled fragment to reach the detection zone is a measure of that fragment's mobility through the gel. By comparing this mobility data to the mobility data of known size standards, the size of each labeled fragment can be determined. Within the detection zone, the DNA fragments are irradiated by a laser beam and excitation/emission of the fluorescent reporters occurs as the fragments move through the zone. Using appropriate filters and a dual-detector system, each of the four nucleotide-specific reporters can be identified on the basis of their distinctive emission spectra.

In another alternative embodiment step 2 of the above-identified method may be modified so that the labeling can occur also with DNA fragments generated by the 3' overhang or blunt end restriction enzymes. In each case the restriction enzymes may be exact end or preferably ambiguous end. To facilitate the use of these additional enzymes, the invention exploits the 3'-exonuclease activity inherent in some DNA polymerases, such as, the Klenow fragment of DNA polymerase I or T7 DNA polymerase or T4 DNA polymerase. When presented with a blunt end or a 3' overhang, these enzymes will remove 3' nucleotides until a 5' overhang is generated. In the absence of deoxynucleoside triphosphates, the enzyme will continue to remove 3' nucleotides creating longer and longer 5' overhangs. In the presence of deoxynucleoside triphosphates, the enzymes adds nucleotides back to the 3' end to generate blunt-ended fragments. The nucleotides added are complementary to the bases in the opposite strand. Thus, blunt ends and 3' overhang ends can be labeled with nucleotide-specific reporters by using the appropriate DNA polymerase and tagged or reporter labeled nucleotides that are accepted by the enzyme. This means that, in the mapping procedure presented here, restriction enzymes that generate blunt ends or 3' overhang ends can be used to cleave the DNA to produce the ends that will be labeled in a nucleotide-specific manner. The mapping procedure is more informative if there is some sequence ambiguity at the ends that are labeled. Thus, in addition to the 5'-ambiguous-end restriction enzymes listed previously, the following ambiguous-blunt-end and 3'-ambiguous-end restriction enzymes are especially useful for this mapping procedure:

| | | | |
|---|---|---|---|
| BgII | —GCCNNNN<br>—CGGN | NGGC—<br>NNNNCCG— | |
| BstXI | —CCANNNNN<br>—GGTN | NTGG—<br>NNNNACC— | |
| Eco57I | —CTGAAGNNNNNNNNNNNNNNNN<br>—GACTTCNNNNNNNNNNNNNNN | NN—<br>NNNN— | |
| GsuI | —CTGGAGNNNNNNNNNNNNNNNN<br>—GACCTCNNNNNNNNNNNNNNN | NN—<br>NNNN— | |
| HaeII | —RGCGC<br>—Y | Y—<br>CGCGR— | R = A or G<br>Y = C or T |
| HincII | —GTY<br>—CAR | RAC—<br>YTG— | R = A or G<br>Y = C or T |
| HphI | —GGTGANNNNNNNN<br>—CCACTNNNNNNN | NN—<br>NNN— | |
| MboII | —GAAGANNNNNNN<br>—CTTCTNNNNNNN | NN—<br>NNN— | |
| MnlI | —CCTCNNNNNNN<br>—GGAGNNNNNNN | NNNN—<br>NNNN— | |
| NlaIII | —NCATG<br>—N | N—<br>GTACN— | |
| NlaIV | —GGN<br>—CCN | NCC—<br>NGG— | |
| NspHI | —RCATG<br>—Y | Y—<br>GTACR— | R = A or G<br>Y = C or T |
| PflMI | —CCANNNN<br>—GGTN | NTGG—<br>NNNNACC— | |
| SfiI | —GGCCNNNN<br>—CCGGN | NGGCC—<br>NNNNCCGG— | |
| TthIIIII | —CAARCANNNNNNNNNNN<br>—GTTYGTNNNNNNNN | NN—<br>NNNN— | R = A or G<br>Y = C or T |

| | | |
|---|---|---|
| XmnI | —GAANN<br>—CTTNN | NNTTC—<br>NNAAG— |

ENHANCED MAPPING PROCEDURE USING SPECIFIC BINDING SUBSTANCES

In an alternative embodiment of this invention, nucleotide specific reporters are attached to the cleaved ends produced by the secondary cleavage. This is true whether 5', 3' or blunt end, ambiguous or exact-end, restriction enzymes are used. This has the advantage that virtually any restriction enzyme may be used for the primary cleavage. It also facilitates the use of this method with larger DNA molecules, i.e., specifically those greater than 50 kilobases. The problem occurring with large DNA molecules is that it is necessary to separate the subset of labeled fragments from the remainder of the DNA to prevent distortion of the DNA fragment pattern caused by overloading the size fractionating gel.

According to this method one member of a specific binding pair is attached to the primary cleaved DNA fragments. For simplicity's sake the cleaved ends to which the one member is attached will be referred to as the "anchor ends". Next, the fragments are cleaved a second time to provide shorter fragments using a different restriction enzyme. The shorter fragments with the anchor ends are separated from the remainder of the DNA fragments by the use of a solid support having the other member (receptor) of the specific binding pair attached to or bound to a solid support, preferably a bead, as will be described hereinafter. A reporter is attached to the free (unattached) end of each shorter separated fragment, separated from its solid support, and finally fractionated according to size with the size and reporter identity being recorded for each shorter fragment.

SOLID SUPPORTS

Many different types of solid supports, although beads are preferable, can be used in this invention. If beads are used, they must be water insoluble and stable to the physical and chemical conditions to which they are subjected during linking of one member (receptor) of the specific binding substance (e.g., avidin) and during elution of the labeled DNA. They must also be capable of being covalently linked to the specific binding substance in a manner which is stable to the elution conditions. It is desirable that the beads exhibit low nonspecific adsorption of nucleic acids under the binding conditions. The beads must be capable of being separated readily from the aqueous medium following binding of DNA fragments, e.g., by settling, centrifugation or application of magnetic field. Beads in the size range 1-300 microns are satisfactory for separation by settling or centrifugation. Beads in the size range 10-100 microns are preferred. In general, beads which have been used heretofore in affinity purifications by hybridization of desired nucleic acids, as described in Moss et al., J. Biol. Chem., 256:12655-8 (1981), Langdale et al., Gene 36:201-210 (1985), Bünemann et al., Nucleic Acids Research, 10:7163-7180 (1982), and Bünemann et al., Nucleic Acids Research 10:7181-7196 (1985), can be used in this invention. A preferred class of beads are composed of organic polymers having terminal amine groups, such as P-100 Bio-Gel aminoethyl polyacrylamide beads of Bio-Rad Co. Other beads which can be used include Sephadex ®G-25, Sephacryl ®S-500, Sephacryl ® S-1000, and Sepharose ®CL-2B, CL-4B and CL-6B, all products of Pharmacia Fine Chemicals, Upsala, Sweden. As described by the manufacturer, Sephadex ® is a bead-formed dextran gel prepared by crosslinking selected dextran fractions with epichlorohydrin. Sephacryl ® beads are formed by crosslinking allyl dextran with N,N'-methylene bisacrylamide. Sepharose ® CL beads are agarose crosslinked with 2,3-dibromopropanol. Also useful is Cellex ®410, a dry cellulose powder available from Bio-Rad Laboratories.

Magnetic beads can also be used, such as the particles described in Hersh, U.S. Pat. No. 3,933,997, Ithakissios U.S. Pat. No. 4,115,534, Forrest et al. U.S. Pat. No. 4,141,687, Mansfield et al., U.S. Pat. No. 4,197,337 and Chagnon, Danish application DK 2374/84. The latter are commercially available under the trade name Biomag ® from Advanced Magnetics. Preferred magnetic beads are the coated $CrO_2$ particles described U.S. Pat. No. 4,661,408 issued to Lau et al. Magnetic particles having an outer layer of a silane compound with functional groups, such as 3-aminopropyl-triethoxysilane, can be utilized for covalent attachment of specific binding substance, either directly or through linear compounds, as taught in the above-cited references.

SPECIFIC BINDING PAIRS

The success of this mapping procedure depends upon efficient separation of fragments with an anchor end from other fragments. The basis of this separation is the strong affinity between the ligand attached to the anchor end and the receptor attached to the solid support.

Preferred specific binding pairs (ligand and receptor) are biotin and avidin or streptavidin. Other pairs which can be used include antibodies and their antigens or haptens; intrinsic factor and vitamin B12; folate binding protein and folic acid; thyroxine binding globulin and thyroxine; sugar and plant lectin, sulfur and mercury, substrate and enzyme and many others. There are at least two reasons for preferring the biotin-streptavidin combination. First, the dissociation constant for the intraction between biotin and avidin or streptavidin is approximately $10^{-15}$, which makes this one of the tightest binding interactions known for this type of ligand-receptor combination. This extremely high affinity means that binding occurs very rapidly, that binding can occur at dilute concentrations, and that the bound complex can be rigorously washed to eliminate nonspecific binding. Second, nucleotides with biotin covalently attached are commercially available.

COVALENT BINDING

Various conventional chemistries can be utilized for covalent attachment of the specific binding substance to the solid support. The chemistry of choice depends upon the functional groups available on the surface of the solid support and/or on the specific binding substance. Specific binding substances containing amine groups can be attached to such solid support having free surface amine groups by use of a difunctional linker such as glutaraldehyde, as described in S. Avrameas, *Immunochemistry* 6, 43 (1969).

Specific binding substances can be covalently attached to Sepharose ®CL-2B and CL-6B, and Sephacryl ®S-500 and S-1000 via cyanogen bromide activation, as taught in the Bünemann et al. and Bünemann references, supra. Specific binding substances can be coupled to Cellex ®410 via epoxy activation as taught in the Moss et al. reference, supra.

METHOD FOR ATTACHING LIGAND TO DNA FRAGMENT ENDS

Enzymatic addition of the ligand can be accomplished by using nucleotides or nucleotide analogs with the ligand covalently attached. These derivatized nucleotides can be incorporated into DNA using enzymes such as DNA polymerases, terminal transferase, or DNA ligases. Restriction enzymes that generate 5'-overhangs create DNA fragment ends that can serve directly as substrate for DNA polymerases. The DNA polymerase will add ligand-bearing nucleotides to the recessed 3' strands in a base-complementary manner. Restriction fragments with blunt ends or 3' overhangs can be used as substrates by using a DNA polymerase with 3'-exonuclease activity. In the absence of nucleotides, the DNA polymerase will remove nucleotides from each 3' end, converting the blunt or 3'-overhang ends into 3'-recessed ends. Then, when ligand-bearing nucleotides are added, the DNA polymerase will attach these nucleotides to the now available 3' ends. Terminal transferase does not require a template strand and therefore can be used to attach ligand-bearing nucleotides directly to any 3' end. In order to use DNA ligases, the ligand-bearing nucleotide must first be incorporated into an oligonucleotide. DNA ligase can then be used to covalently attach the oligonucleotide to any DNA fragment end.

ABILITY TO ELUTE LABELED FRAGMENTS FROM SOLID SUPPORT

One method for eluting the labeled fragments from the solid support takes advantage of the double-stranded nature of DNA. First, the ligands are attached only to the 3' strand of each anchor end. When these fragments are bound to the solid support, the opposite strand remains attached to the ligand-bearing strand because of the base-pairing of DNA. Then, the labeled reporter is added only to the 3' strand of each free end. This means that the binding ligand is on one strand and the reporter is on the opposite strand. Thus, the labeled strand can be eluted by any treatment that denatures the DNA double helix without regard to the ligand-receptor interaction. For example, incubation in formamide at 65°-70° C. is a mild treatment that will denature DNA and elute the labeled strands. Another method for eluting the labeled fragments would be to incubate under conditions that destabilize the ligand-receptor binding interaction.

SUMMARY OF ENHANCED MAPPING PROCEDURE (1) Cleave DNA segment made up of duplex strands of nucleotides in a sequence-specific manner, i.e., with a restriction enzyme (one or more of the 5',3', or blunt, exact or ambiguous end, restriction enzymes), to produce DNA fragments.

(2) Derivatize the cleaved ends of the DNA fragments by attaching an appropriate ligand so that fragments with ligand-bearing ends can be physically separated from other fragments. One way to do this is to attach a biotin-labeled nucleotide or nucleotides to the 3' strand at each end of each fragment. These derivatized ends will be referred to as anchor ends.

(3) Cleave the DNA again using an agent that has a different sequence specificity than the initial cleavage, e.g., by using a different restriction enzyme. In order to take advantage of nucleotide-specific reporters, the preferred cleavage agent is one or more of the 5'-ambiguous-end, ambiguous-blunt-end, or 3'-ambiguous-end restriction enzymes.

(4) Physically separate DNA fragments that have at least one anchor end from fragments that do not. If biotin is used at the anchor ends then the separation can be accomplished by using a solid support coated with streptavidin. The strong affinity between biotin and streptavidin will cause the fragments with an anchor end to bind to the solid support and the other fragments can be washed away. By the proper choice of cleavage agents in steps 1 and 3, most fragments attached to the solid support will have one anchor end and one free end.

(5) Attach a reporter or reporters to the free end of each anchored fragment. For example, use a DNA polymerase to attach nucleotide-specific fluorescent tags to the 3' strand at each free end.

(6) Separate the labeled fragments or strands from the solid support. For the case where biotin has been attached to the 3' strand of each anchor end, the opposite strand can be released from the solid support by denaturing the duplex DNA.

(7) Fractionate the labeled fragments by size, e.g., by using gel electrophoresis. Record the size and reporter identity of each labeled fragment. This collection of data is a fingerprint of the original DNA sample that can be used to test for similarity to other DNA samples.

The order of steps (3), (4), and (5) could be varied and still result in the same collection of labeled fragments. The attachment of reporters could be performed before the derivatized fragments are bound to the solid support. In this case, all of the ends generated by the second cleavage are labeled with reporters. Although they are reporter-labeled, fragments that do not have at least one anchor end will not interfere with subsequent analysis because they can be washed away when fragments with an anchor end are bound to the solid support. Alternatively, the derivatized fragments could be bound to the solid support before the secondary cleavage. In this case, all the DNA fragments bind to the solid support. Secondary cleavage to produce shorter fragments can be accomplished by incubating the bound DNA with a second restriction enzyme or enzymes. Only short fragments that retain at least one anchor end remain attached to the solid support during washing steps. Thus, the same collection of DNA fragments is available for reporter labeling as in the summary procedure outlined above.

The end result of these procedures is to characterize a DNA segment with a list of fragments where each fragment is identified by both its size and its 3' terminal bases. Fragment lists of different DNA segments can be compared, searching for fragments that are identical in size and terminal base identity. A significant number of matching fragments indicates that two DNA segments are related. Inclusion of the 3' terminal base(s) identity adds significantly to the amount of information in each fragment list. This means that comparisons of DNA segments can be accomplished more rapidly and accurately than with lists that rely solely on fragment size. Thus, if fragments from large genomes are being compared, the methods considerably enhances the confidence with which overlaps can be determined.

The Du Pont Genesis 2000 ™ DNA Sequencer and the nucleotide-specific reporters preferably used therewith are fully described in a patent application, Ser. No. 057,566, filed June 12, 1987 and entitled "Method System and Reagents for DNA Sequencing" by Prober et al. In order to provide a full disclosure of these reporter labeling techniques, the teachings of Prober et al. are incorporated herein by reference. In addition, the Prober et al. teachings are described herein. Prober et al. teach chain terminator labeling in a modification of the Sanger DNA sequencing method.

The classical Sanger method uses a primer, DNA template, DNA polymerase I (Klenow fragment), three unlabeled deoxynucleotides and one radiolabeled deoxynucleotide in four reaction vessels that each contain one of four 2′,3′-dideoxynucleotides, which correspond to the four DNA bases (A,C,T,G). Appropriate reaction conditions are created which allow the polymerase to copy the template by adding nucleotides to the 3′ end of the primer. A multitude of reactions occur simultaneously on many primer copies to produce DNA fragments of varying length which all contain the radiolabel at appropriate nucleotides in each fragment, and which also irreversibly terminate in one of the four dideoxynucleotides. This set of fragments is typically separated on a polyacrylamide slab electrophoresis gel in four lanes, one lane corresponding to each of the four dideoxynucleotide reaction mixtures. After the fragments have been separated, a photosensitive film is placed on the gel, exposed under appropriate conditions, and a DNA sequence is inferred from reading the pattern of bands on the film in order of their appearance in the four lanes from the bottom of the gel.

The modifications to the Sanger method according to Prober et al., include omitting the radiolabeled nucleotide and substituting reporter-labeled chain terminators for the unlabeled 2′,3′-dideoxynucleotides. Reaction mixtures will now contain fragments which are irreversibly labeled on their 3′ ends with an appropriate reporter that corresponds to each of four DNA bases. The reaction mixtures are combined and electrophoretically separated.

As described by Prober et al the fluorescent detector includes a laser whose light is directed at the excitation wavelength of the fluorophores to a specific region of the electrophoresis gel. As the DNA fragments move through the specific region, their reporter is excited. The light beam from the laser is passed through an excitation filter and focussing lens prior to striking the gel. The light emitted by the fluorescent species is collected as described in a copending application by Robinson et al., Serial No. 060,874, filed June 12, 1987, whose disclosure is incorporated herein by reference, by a pair of modules positioned above and below a plane in which the reporter exciting beam may scan multiple lanes on a gel. Each detection module comprises a photomultiplier tube having a wide entrance area on a separate wavelength selective filter positioned between its PMT and the fluorescent species in the gel. These filters are interferences filters having complimentary transmission band characteristics which simulate the dichroic filter action. The filters permit the PMT's to generate signals that vary in amplitude in different senses as a function of the nature of the species. One filter largely passes the lower emission wavelengths and rejects the high emission wavelengths while the other filter does precisely the reverse. Transmission filters may be used with each interference filter to reject light from off-axis angles greater than a predetermined angle. The wavelength filters have roughly complementary transmission vs. wavelength characteristics in the emission region of the four dyes, with the transition wavelengths occurring near the center of the species radiant energy.

The electrical signals from the detectors are then passed via respective preamplifiers to a A/D converters and thence to a computer which calculates the ratio of the two signal functions. The wavelength filters modulate the intensity of the signals representing the fluorophores in each of the different wavelength bands according to wavelength. The magnitude of the ratio signal is indicative of the identity of the species and tend to fall into groupings or clusters which are uniquely indicative of each reporter. This identity is true whether the above described Genesis 2000 ™ detector or any other fluorescence detection system is used.

Other reporters can be used as well, but will not be discussed since the particular reporter used is immaterial to the subject invention. The information obtained using the fluorescent tag described above, or any other reporter is that of the time required for the reagents to reach the detection zone and the identity of the labeled nucleotides complementary to those in the 5′ overhang. This information is obtained for each fragment and, as described above, greatly facilitates the task of ascertaining the relateness of different DNA segments. To delineate the structural scope and rationale of the reporter-labeled chain terminators used herein, it is useful to break the structure down into five components. A fluorescence-labeled chain terminator, for example, contains (i) a triphosphate part (ii) a "sugar" part, (iii) a heterocyclic base part, (iv) a linker part, and (v) a reporter part, where the reporter is a fluorescent compound.

It should be apparent from the preceding description that the term "chain terminator" is generic to the process of DNA sequencing with the Sanger methodology. The improved process of Prober et al. utilizes more specialized varieties of chain terminators which advantageously also have a reporter attached to them. These novel compounds can be differentiated from generic chain terminators in that the latter compounds typically contain only the triphosphate (i), "sugar" (ii), and heterocyclic base (iii) parts outlined above. The chain terminators of Prober et al. will be termed "reporter-labeled chain terminators," and typically contain all five parts described hereinafter. The triphosphate, sugar, and heterocyclic base parts are well known and need not be discussed further.

The linker which couples the reporter to the base may be simply an amino group alone or a chain with a backbone containing such atoms as carbon, nitrogen, oxygen or sulfur.

The linker is preferably an alkynylamino group in which one end of the triple bond is attached to an amine through a substituted or unsubstituted diradical moiety, $R_1$, of 1-20 atoms; the other end of the triple bond is covalently attached to the heterocyclic base at the 5-position for pyrimidines or the 7-position (purine numbering) for the 7-deazapurines. The amine nitrogen of the alkynylamino group is attached to a reactive functional group (e.g., carbonyl) on the fluorescent label. The linker must not significantly interfere with binding to or incorporation by the DNA polymerase. The diradical moiety can be straight-chained alkylene, $C_1$–$C_{20}$, optionally containing within the chain double bonds, triple bonds, aryl groups or heteratoms such a N, O or S. The heteratoms can be part of such functional groups as ethers, thioethers, esters, amines or amides. Substituents on the diradical moiety can include $C_1$–$C_{20}$; most preferably the diradical is —$CH_2$—. A more detailed description of the linkers most appropriate for use in the reporter-labeled chain terminators of this invention can be found in copending patent application by Hobbs et al., Ser. No. 057,565, filed June 12, 1987, and entitled Alkynylamino-Nucleotides.

REPORTER PART

The preceding disclosure emphasizes the utility of a detection means which is particularly adapted to measurement of closely spaced spectra preferably of a set of fluorescent reporters as the emitting species. However, other species which emit radiation with closely spaced spectra can also be used to label DNA fragments. Several criteria can be identified for selection of appropriate reporter species to perform the methods of this invention. These criteria include:

efficient excitation by a monochromatic source and a strong, distinguishable emission response;

presence of a chemically reactive functional group capable of covalent attachment either directly or indirectly to nucleotide chain terminators or their analogs;

relatively small mass to minimize perturbation of steric relationships in oligonucleotide fragments;

charge and size characteristics which resemble those in other members of a chosen group or set of reporters selected for differentiation of chain terminators;

stability in a wide range of sample preparation, reaction and fragment separation conditions of pH, ionic strength, and temperature with respect to physical integrity and detection characteristics;

properties which have minimal deleterious effect on the production of or separation of DNA sequencing fragments.

Appropriate reporter species may be found in several categories of materials which can function with the above-mentioned properties. Among them are chromophores, fluorophores, chemiluminescers, spin labels, and electron dense materials. Detection of each of these species of materials can also be accomplished by a variety of means. For example, fluorescent species emissions can be detected as discussed previously in a manner that differentiates spectral distributions. In alternate fluorescent detection systems, additional species properties such as polarization and differential time-resolution can be employed to uniquely identify fragments having labeled DNA chain terminators corresponding to each base. The detection means selected can be optimized by known methods to maximize the signal-to-noise ratio and achieve acceptable sensitivity by minimizing background or extraneous signals. The unique properties and advantages of Prober et al. are achieved by coupling an appropriate detection means with the reporter-labeled chain terminator in sequencing DNA.

In similar fashion, conventional photometry can be used to detect chromophores meeting the requirements of reporters in the methods of Prober et al. Four unique chromophores can be selected, which may also possess fluorescent properties, to be incorporated on chain terminators to introduce reporters detectable by a number of means, including absorption and photon counting spectrophotometry. A typical example of chromophores which may be useful are 2,4-dinitrophenol and its derivatives. Appropriate substitutions can result in different emission characteristics under a given set of conditions that are similar, which allows their detection by the apparatus previously described with little modification.

Luminescent reporters are differentiated from fluorescent reporters in the period of time required to re-emit incident radiation. Fluorescent reporters generally re-emit absorbed incident energy on the order of $10^{-8}$ to $10^{-3}$ seconds. The term "phosphorescent" is also often used to refer to compounds which are luminescent and the terms are generally used interchangeably. These compounds take longer to re-emit incident absorbed energy than fluorescent compounds Typical luminescent reporters are derivatives of 2,2'-dihydroxybiphenyl-5,-5'-diacetic acid for 2,2'-dihydroxy-3,3'-dimethoxybiphenyl-5,5'-diacetic acid, 2,2'-dihydroxybiphenyl-5,5'-dialanine, 2,2'-dihydroxybiphenyl-5,5'-diethylamine, etc.

Additional reporter species can be covalently attached to chain terminators that serve as electron dense reagents, such as colloidal gold particles. These materials can be used in an imaging system capable of detecting small changes in transmissive properties of light incident on an electrophoresis gel lane. Spin labels may also be used with appropriate detectors to uniquely label each chain terminator to make base assignments. The complexity of detection means in these instances may require the simplification of maintaining separate samples for each reporter-labeled chain terminator, rather than combining them into one sample before subjecting the sample(s) to a separation means.

It should be apparent to one skilled in the art that appropriate means to detect a combination of the above mentioned reporters can be readily devised to further differentiate the four reporter-labeled nucleotide chain terminators in a given system. This is especially applicable with the compounds covalently attached to chain terminators having both strong fluorescent and absorption properties. However, any combination of the above reporters which are selected for use according to the desirable properties already disclosed, can be used in systems having a complementary array of detection means.

In the more specific instance of the preferred embodiment of Prober et al., the fluorescent part provides detectable, emitted radiation following excitation by absorption of energy from an appropriate source such an argon ion laser. It is desirable to have a unique fluorescent reporter for each DNA base encountered in sequencing applications and a set of four distinguishable fluorescent reporters is generally adequate.

A family of reporters which are useful in the DNA sequencing methods of Prober et al. was deviced especially for this purpose and is based on the known dye 9-carboxyethyl-6-hydroxy-3-oxo-3H-xanthene. Other dyes are known which are also derived from this parent compound. S. Biggs et al., *J. Chem. Soc.*, 123, 2934–2943 (1923) disclosed the preparation of several succinylfluorescein derivatives presumed to have bromine substitutions at either two or four (succinyleosin) positions in the resorcinol ring structure. Additional derivatives bearing dinitro and tetranitro substituents on succinylfluorescein were also prepared. These dyes were apparently prepared by simpler and more efficient methods over previous processes. However, no relationship of these dyes was disclosed and no significant characterization of their physical properties, including their emission spectra, was performed. This family of fluorescent reporters found useful for DNA sequencing by the methods of Prober et al. has the general structure

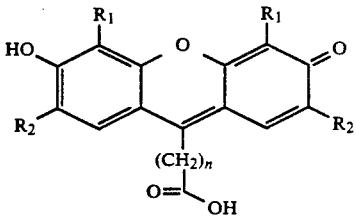

where n is 2 or 3 and $R_1$ and $R_2$ are H, lower alkyl, lower alkoxy, halo, and cyano. These materials are easily prepared by condensing either succinic or glutaric anhydride with the appropriate substituted resorcinol in methanesulfonic acid. This is a modification of the procedure reported by Biggs et al. for the preparation of the parent compound.

P. Khanna et al. [U.S. Pat. No. 4,481,136 (1984)] have described a class of compounds that include the structure 1 when $R_2$ is alkyl and $R_1$ is H and their use in the preparation of fluorescent antigen conjugates. While their individual use in fluorescent immunoassays is demonstrated, there is no indication of a utility requiring a family of such dyes or of any application to DNA sequencing.

The xanthene dyes are understood to be capable of existing in several different, generally interconvertible molecular forms. These forms, indicated below for the parent (1, n=2, $R_1=R_2=H$) are designated the quino-, delta-, spiro-, and leuco-, forms. The form that is observed in a given situation will be determined by the nature of n, $R_1$, and $R_2$, and by conditions such as temperature, solvent, pH, and crystal form. For clarity and convenience, only the quino- form will be used in naming and drawing structures.

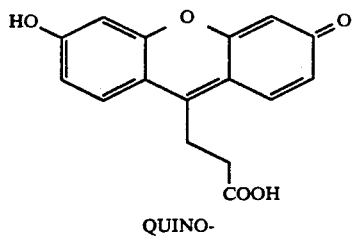

QUINO-

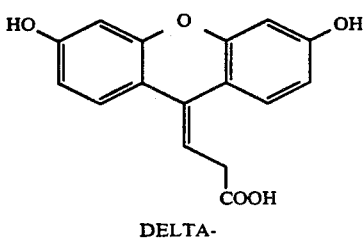

DELTA-

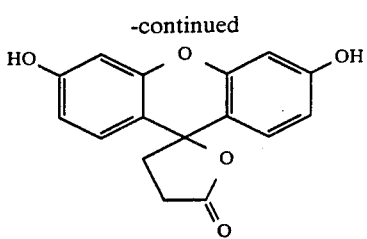

SPIRO-

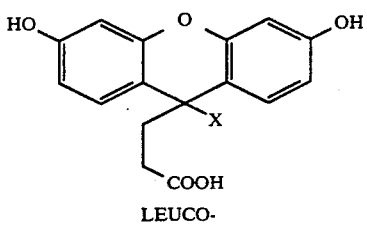

LEUCO-

The actual fluorescent species is the dianion 2, formally derived from the quino- form. This species will generally predominate in aqueous solution above pH 7. The dianion derived from the parent dye (n=2, $R_1=R_2=H$) is very well suited to excitation by an argon ion laster operating at 486 nm. At pH 8.2 this species shows an absorption maximum at 487 nm with an absorption coefficient at about 72,600. The species emits at 505 nm with an efficiency comparable to that of fluorescein (quantum yield about 0.9).

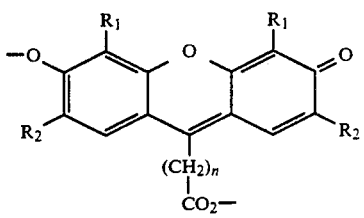

A set of four distinguishable fluorescent dyes can be generated by including small changes in the emission maximum of the parent chromophore through changes in the nature of the substituents $R_1$ and $R_2$. The correspondingly small differences in the absorption spectra maintain efficient excitation with an argon ion laser operated at 486 nm. By limiting the choice of $R_1$ and $R_2$ to relatively small substituents carrying no net charge one can insure that differential effects on the electrophoretic mobility, when the dyes are attached to DNA fragments, will be small.

A preferred set of such dyes suitable for DNA sequencing is: (structure 1, n=2, 1) $R_1=R_2=H$, abs. 486 nm, emis. 505 hm; 2) $R_1=H$, $R_2=CH_3$, abs. 494 nm, emis. 512 nm; 3) $R_1=CH_3$, $R_2=H$, abs. 500 nm, emis. 519 nm; 4) $R_1=R_2=CH_3$, abs. 509 nm, emis. 526 nm. The dye with the longest wavelength absorption maxima shows an excitation efficiency of about 50%. These four dyes are easily detected and distinguished at concentrations suitable for DNA sequencing.

DYE ATTACHMENT TO CHAIN TERMINATORS

Covalent attachment of these xanthene dyes is made through the carboxylic acid functionality, via an amide bond with a linker amine group. It is useful to introduce chemical protecting groups to lock the dyes into a suitable form and minimize side-reactions during coupling.

Reaction of the dye (1) with alkyl or aryl acide anhydride (R') in pyridine, followed by treatment with alkyl alcohol (R") in excess, affords a new composition, the protected dye (3) which bears acyloxy groups at the 3- and 6-positions and alkoxy group (derived from the alcohol) at the 9-position. Compounds where the acyl group is acetyl and the alkoxy group is ethoxy are easy to prepare and show good stability, crystallinity, and organic solubility. Brief treatment with concentrated aqueous ammonia regenerates the free dye.

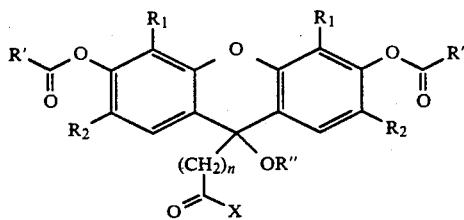

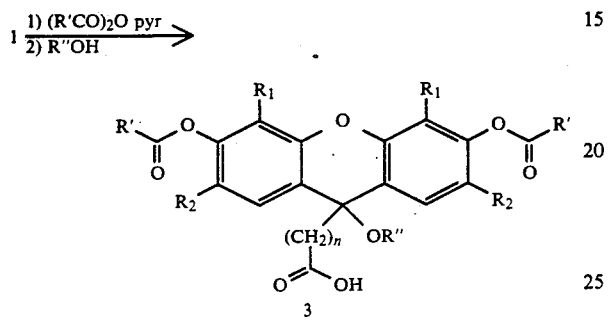

The protected dyes (3) may be coupled to amines via the carboxyl group using any one of a number of standard procedures. Amide bonds are preferred because they are stable, easy to form, and compatible with aqueous systems. The active species in these procedures is generally an intermediate of structure 4 where -X is a good leaving group.

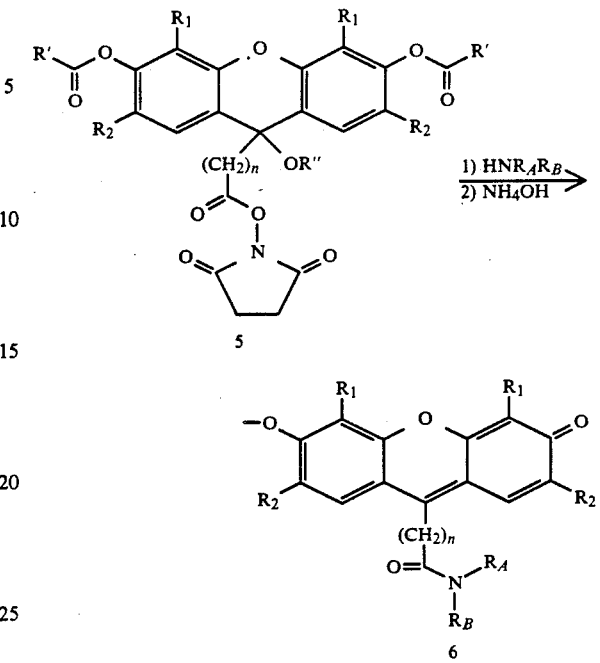

These active species are usually generated and coupled in situ but in some cases the intermediates can be isolated and purified. One particularly useful class of isolable, activated intermediates is the NHS esters 5. The compounds are easily prepared by treating the protected dyes 3 with an appropriate carbodiimide, such as N,N-dicyclohexylcarbodiimide, or preferably 1-(3-dimethylaminopropyl)-3-ethylcarbodiimide hydrochloride, in the presence of N-hydroxysuccinimide. They are stable, highly crystalline compounds which will react cleanly with primary secondary amines in a variety of solvents. The primary and secondary amines are contributed by the material of interest to be analyzed in the system of this invention. These materials are typically dideoxynucleotides or their analogs containing the desired deazapurine and pyrimidine bases useful in the modified Sanger DNA chain extension protocol.

The NHS esters 5 may be used directly for coupling to a wide variety of second amines Deprotection of the product with aqueous ammonia affords a dye-labeled amine derivative 6 which shows full fluorescence intensity.

Coupling of an NHS ester 5 to primary amines is rapid and clean but deprotection generally affords a labeled amine which displays reduced fluorescence intensity. This is attributable to a partial equilibration of the fluorescent product 7a to the non-fluorescent spirolactam form 7b. The degree of equilibration is solvent, pH, and amine dependent. This problem can be alleviated by inserting a spacer between the dye and the amine. The spacer can be selected from diamines, diacids, or from molecules bearing secondary amines and carboxylic acids. Preferred spacers contain reactive amines which can form amide bonds with dye carboxyl groups. The spacer is associated primarily with the reporters, particularly the fluorescent dyes, and it functions to move the reactive amine away from the dye in order to prevent cyclization to the spirolactam form. It is also consistent with observation that the spacer functions to extend the dye farther from the DNA polymerase active site. This extension may improve the incorporation of reporter-labeled chain terminators into DNA fragments.

In contrast, the coupling of an NHS ester 5 to a preferred secondary amine affords a species which does not show appreciable cyclization to the spirolactam form but which carries a carboxylic acid for activation and coupling to the amine of interest.

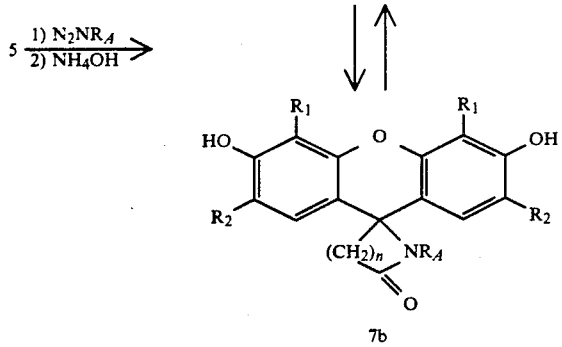

For example, a simple and effective spacer can be constructed from the amino acid sarcosine. Coupling of an NHS ester (5) to sarcosine benzyl ester followed by removal of the benzyl ester affords a carboxylic acid of the structure 8. As with the protected dyes (3) themselves, these carboxylic acids (8) can be coupled to amines using any one of a number of standard methods. Again, NHS esters of the structure 9 are isolable and particularly useful in this context.

Coupling of NHS esters 9 to amines followed by deprotection in aqueous ammonia affords dye-labeled amine derivatives of general structure 10 which are fully fluorescent.

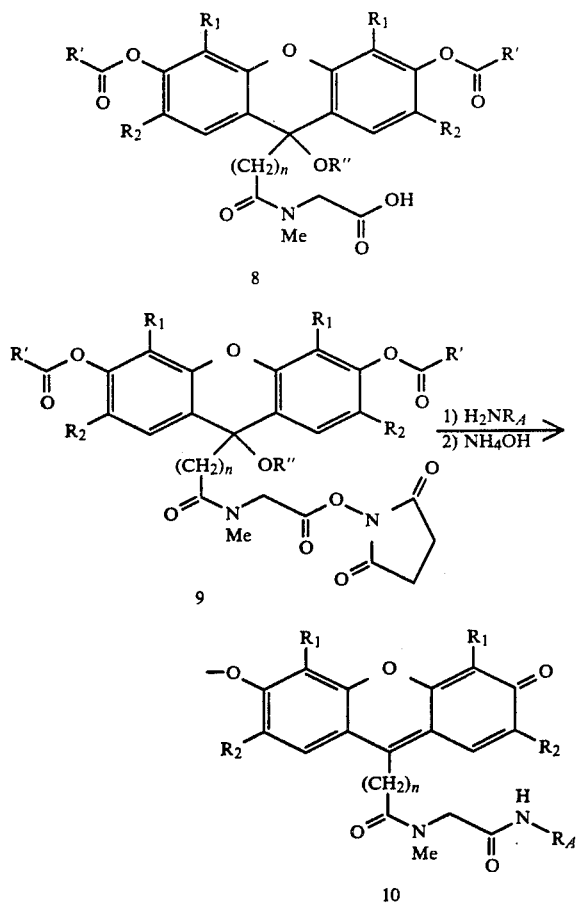

As a general rule, it would be preferable to design or obtain a material of interest that contained a primary amine, which could be reached with an appropriate spacer. The insertion of the spacer is believed to prevent cyclization reactions. Secondary amines can be used but do not react as rapidly or as efficiently as primary amines.

A representative fluorescence-labeled-chain-terminator is 11. This material can be constructed via a convergent route. 2′,3′-Dideoxyuridine is prepared from commercially available 2′-deoxyuridine in 5 steps [K. E. Pfitzner et al., J. Org. Chem., 29, 1508–1511 (1964)]. The 5′-triphosphate is prepared directly adapting the one-vessel procedure of J. L. Ruth et al., Mol. Pharmacol., 20, 415–422 (1981). A 3-amino-1-propen-1-yl linker is appended to the 5-position on the heterocyclie-base through an adaptation of the sequence of reactions described by P. Langer et al., Proc. Nat. Acad. Sci U.S.A., 78, 6633 (1981) and Eur. Pat. Appl. #82301804.9 (1982). Reaction of 5-(3-amino-1-propen-1yl)-2′,3′-dideoxyuridine-5′-triphosphate with the NHS ester 9 (N=2, $R_1=R_2=H$) followed by deprotection by brief treatment with aqueous ammonia affords the novel fluorescence-labeled chain-terminator 11.

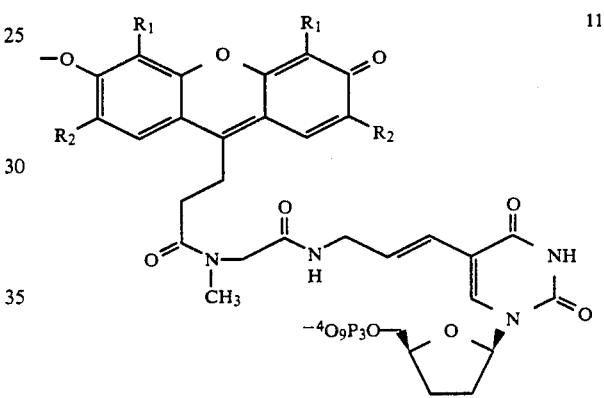

Compound 11 can substitute for ddTTP in the modified Sanger protocol. A full set of four chain terminators can consist of 11 and three analogs with different heterocyclic base and fluorescent parts. Preparation of the three analogs to substitute for the remaining non-labeled chain terminators of the modified Sanger protocol involves replacement of the heterocyclic base part of 11 (uracil) by cytosine (for ddCTP), 7-deazaadenine (for ddATP), and 7-deazaguanine (for ddGTP). The fluorescent part can be altered by changing the aromatic substituents $R_1$ and $R_2$ from both H (in 11) to, respectively, $CH_3$ and H, H and $CH_3$ and both $CH_3$. The compounds are prepared through routes similar to that described for 11.

It has been found that replacement of the 3-amino-1-propen-1-yl linker with a 3-amino-1-propyn-1-yl linker affords functionally equivalent reporter-labeled chain terminators that can be prepared more easily. The use of a propynyl linker allows preparation of more stable reporter-labeled chain terminators in higher yield than those prepared with the propenyl linker. Another advantage is that the propynyl linker is more regioselectively attached to nucleotide bases than the propenyl linker.

Therefore, the preferred reporter-labeled chain terminators for use in the Sanger chain extension method as modified by this invention are 12, 13, 14, and 15.

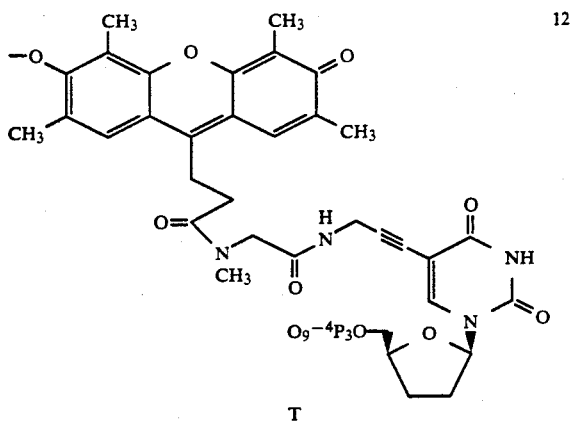

T

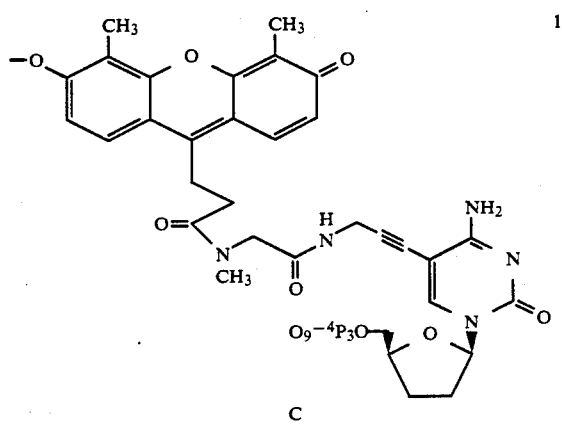

C

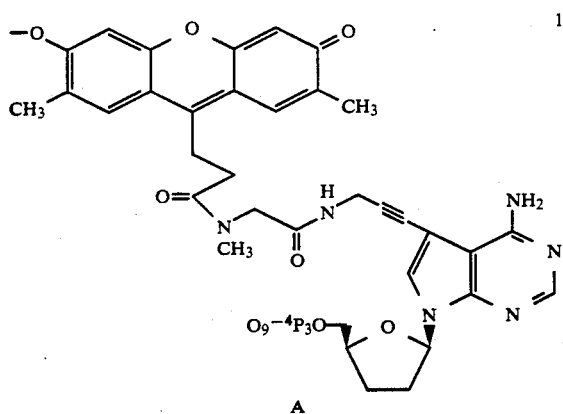

A

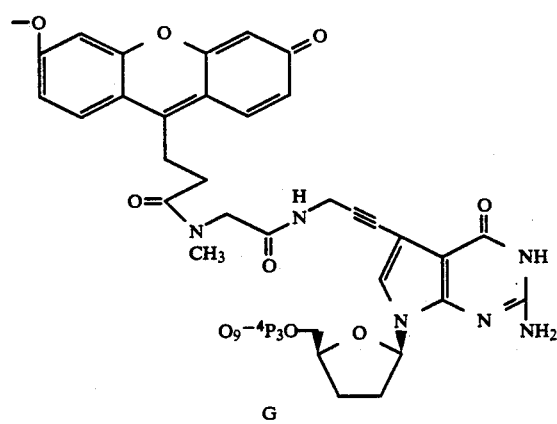

G

Further, it is expected that once a fluorescent dye is covalently coupled to a deazapurine or pyrimidine base through a linker and optional spacer, that its nominal emission maximum will shift toward a somewhat longer wavelength. This effect depends to an extent upon the nature of the base and upon the conditions of measurement such as pH, ionic strength, solvent, separation medium etc. Alternatively, one factor which does not appear to influence the emission characteristics of the fluorophores is the nature of the adjacent nucleosides in the DNA fragment containing the fluorescently-labeled chain terminator. Emissions of a given fluorophore appear to remain constant when its chain terminator is enzymatically coupled next to any of the pyrimidines and purines. For example, the reporter-labeled chain terminators disclosed above have fluorophores which emit maximally at 515 nm (12), 524 nm (14), 530 nm (13), and 536 nm (15), after 488 nm excitation. Under similar conditions of measurement, these fluorophores in the uncoupled state free in solution, had nominal emission maxima of 505 nm, 512 nm, 519 nm, and 526 nm, respectively. These shifts in emission maxima are easily measured and within routine experimentation to determine. Characterization of this distribution of emission maxima, in turn, allows one to select the desired reflection/transmission characteristic of the dichroic filter or its equivalent in the system of this invention.

EXPERIMENTAL

The following examples are offered by way of illustration and not by way of limitation.

All temperatures are in degrees centigrade. (25° refers to ambient or room temperature). All parts and percentages not otherwise indicated are by weight, except for mixtures of liquids which are by volume. The following abbreviations are employed: DMF-dimethylformamide; DMSO-dimethylsulfoxide; NHTFA-trifluoroacetamido group; TEAB-triethylammonium bicarbonate; Tris-tris(hydroxymethyl)aminomethane; SF-succinylfluorescein; NMR-nuclear magnetic resonance spectrum; IR-infrared spectrum; UV-ultraviolet spectrum or detection; TLC-thin layer chromatography on silica gel; HPLC-high pressure liquid chromatography; GC-gas chromatography; mp-melting point; mp d-melting point with decomposition; bp-boiling point. In reporting NMR data, chemical shifts are given in ppm and coupling constants (J) are given in Hertz. All melting points are uncorrected. Ion exchange resins were washed with appropriate aqueous and organic solvents prior to use. The identity of all compounds described herein was established by appropriate spectroscopic and analytical techniques. Unless otherwise noted, purification by chromatography on silica gel was performed as described by Still et al., J. Org. Chem., 43, 2923–2926 (1978).

EXAMPLE 1

Preparation of a 505 nm fluorescent-labeled spacer-activated ester intermediate

A. Preparation of 9-(Carboxyethylidene)-3,6-dihydroxy-9H-xanthene (SF-505)

Resorcinol (33.0 g, 0.300 mol) and succinic anhydride (30.0 g, 0.300 mol) were placed in a round bottomed flask and purged with nitrogen. Methanesulfonic acid (150 mL) was added and the solution was stirred at 65° C. for 2 hours under an atmosphere of nitrogen. The reaction mixture was added dropwise to rapidly stirred, ice-cooled water (1L) with simultaneous addition of 50% aqueous sodium hydroxide to maintain pH 2.5+/0.5. The product which appeared as a granular precipitate was collected by filtration and rinsed with water (3×100 mL) then acetone (3×100 mL). The product was air-dried then vacuum-dried (vacuum oven) at 110° C. for 18 hours to afford a dark red powder (37.7 g, 88%).

An analytical sample was prepared by dissolving 1.0 g of product in 25 mL of hot 0.3N HCl. The precipitate which formed on cooling was removed by filtration and discarded. Dilute aqueous sodium hydroxide was added to raise the pH to 1.25. The resulting precipitate was collected by filtration, rinsed with water, air-dried, then vacuum-dried over $P_2O_5$ at 140° C. for 36 hours. Anal: Calc. [C(16)H(12)O(5)] C 67.60, H 4.26. Found: C 67.37, H 4.34, 0.52% water (K-F). NMR (DMSO-$d_6$): (mostly spirolactone form) $\delta$2.690 (t, J=8.6 hz, 2H); 3.070 (t, J=8.6 hz, 2H), 6.530 (d, J=1.8 hz, 2H); 6.676 (dd, J=8.7, 1.8 hz, 2H), 7.432 (d, J=8.7, 1.8 hz, 2H), 7.432 (d, J=8.7 hz, 2H), and 9.964 (s, 2H). Vis. abs. (pH 8.2; 50 mM aq Tris/HCl): max 486 nm (72,600).

B. Preparation of 9-(2-Carboxyethyl)-3,6-diacetoxy-9-ethoxy-9H-xanthene (Ac2EtSF-505)

SF-505 (29.3 g, 103 mmol) was added to ice-cold acetic anhydride (500 mL) followed by pyridine (100 mL). The mixture was stirred in ice for 20 minutes then added over 20 minutes to rapidly stirred, ice-cold water (7 L). After stirring for an additional 30 minutes, the intermediate product was filtered and resuspended in water (4 L) and stirred for another 30 minutes. The solid was collected by filtration, dissolved in absolute ethanol (1 L), and refluxed for 45 minutes. The solution was concentrated on a rotary evaporator to 200 mL which resulted in crystallization. The product was collected by filtration, air-dried, then vacuum-dried to afford pale-orange microcrystals (21.9 g, 51%).

Recrystallization from methylene chloride/cyclohexane gave colorless microcrystals. M.p.: 142°-143° C. Anal: Calc. [C(22)H(22)O(8)] C 6.63.76, H 5.35. Found: C 63.58, H 5.39. NMR (DMSO-$d_6$): $\delta$1.035 (t, J=6.9 hz, 3H), 1.667 (m, 2H), 2.232 (m, 2H), 2.294 (s, 6H), 2.888 (q, J=6.9 hz, 2H), 7.0–7.1 (m, 4H), and 7.575 (d, J=9.1 hz, 2H).

C. Preparation of 9-(2-(N-Succinimidyloxycarbonyl))ethyl)-3,6-diacetoxy-9-ethoxy-9H-xanthene (Ac2EtSF-505-NHS)

Ac2EtSF-505 (10.4 g, 25.1 mmol) was mixed with methylene chloride (300 mL) and 1-(3-dimethylaminopropyl)-3-ethylcarbodiimide hydrochloride (9.70 g, 50.6 mmol) and N-hydroxysuccinimide (4.32 g, 37.5 mmol) were added. The mixture was stirred for one hour and then washed with water (5×50 mL). The combined aqueous layers were back extracted with methylene chloride (50 mL) and the pooled organic layers were dried over sodium sulfate and stripped down. Trituration with ethanol (75 mL) followed by filtration and air-drying afforded the crude product as a light yellow solid (c. 10 g). This material was dissolved in methylene chloride (50 mL) and cyclohexane (50 mL) was added. One teaspoon of charcoal was added, the mixture was filtered, and the product was brought down with an additional portion of cyclohexane (100 mL). Collection by filtration, air-drying, and vacuum-drying afforded colorless crystals (6.94 g, 54%).

A second crystallization from ethanol afforded an analytical sample. M.p.: 162°-3° C. Anal: Calc. [C(26)H(25)N(1)O(10)] C 61.05, H, 4.93, N 2.74. Found: C 60.78, H 5.01, N 2.65. NMR (DMSO-$d_6$): $\delta$1.056 (t, J=7.0 hz, 3H), 2.4–2.1 (m, 4H), 2.293 (s, 6H), 2.757 (s, 4H), 2.922 (q, J=7.0 hz, 2H), 7.069 (m, 4H), and 7.617 (p d, J=9.1 hz, 2H),

D. Preparation of 9-(2-(N-methyl-N-(benzyloxycarbonylmethyl)carboxamido)ethyl-3,6-diacetoxy-9-ethoxy-9H-xanthene (Ac2EtSF-505-Sar-OBn)

To a solution of sarcosine benzyl ester* (1.13 g, 6.31 mmol) in methylene chloride (50 mL) was added Ac-2EtSF-505-NHS (2.58 g, 5.05 mmol) and 5% aq sodium bicarbonate solution (30 mL). The two-phase mixture was stirred rapidly for 20 hours. The layers were separated and the organic layer washed with 3×15 mL water, dried over sodium sulfate, and concentrated to 25 mL. The solution was diluted to 150 mL with cyclohexane, charcoal-treated, and reduced to 75 mL under a stream of nitrogen resulting in the precipitation of the product. The supernatant was decanted away and the residue coevaporated with methylene chloride to afford a colorless foam (1.70 g, 58%).

* Sarcosine benzyl ester p-tosylate salt (Adams Chemical Co.) was taken up in methylene chloride and washed repeatedly with 5% aqueous sodium bicarbonate, then water washed, dried over sodium sulfate, and stripped down.

Extensive vacuum-drying afforded an analytical sample. Anal: Calc. [C(32)H(33)N(1)O(9)] C66.77, H 5.78, N 2.43. Found: C 66.66, H 5.89, N 2.25. NMR (DMSO-$d_6$): (Shows 5:2 mixture of amide bond rotamers.) $\delta$ (major and minor) 1.040 and 1.018 (t, J=6.7 hz, 3H), 1.789 and 1.670 (m, 2H), 2.211 (m, 2H), 2.290 and 2.276 (s, 6H), 2.713 and 2.695 (s, 3H), 2.893 (q, J=6.7 hz, 2H), 3.963 (s, 2H), 5.075 and 5.039 (s, 2H), 7.044 (m, 4H), 7.324 (m, 5H), and 7.573 and 7.516 (p d, J=9.2 hz, 2H).

E. Preparation of 9-(2-(N-Methyl-N-(N'-succinimidyloxycarbonylmethyl)carboxamido)ethyl)-3,6-diacetoxy-9-ethoxy-9H-xanthene (Ac2EtSF-505-Sar-NHS)

To a solution of Ac2ETSF-505-Sar-OBn (1.55 g, 2.69 mmol) in absolute ethanol (60 mL) was added 10% palladium on carbon (0.15 g). The mixture was stirred under balloon pressure of hydrogen for 30 minutes. The catalyst was removed by filtration and the ethanol stripped off to afford a syrupy residue.

This residue was dissolved in methylene chloride (85 mL) and N-hydroxysuccinimide (0.495 g, 4.30 mmol) and 1-(3-dimethylaminopropyl)-3-ethylcarbodiimide hydrochloride (1.12 g, 5.84 mmol) were added (4×25 mL). The solution was concentrated to 25 mL, diluted to 175 mL with cyclohexane, charcoal treated, and reduced in volume to 75 mL under a stream of nitrogen. The solid product was collected by filtration, air-dried, and vacuum-dried to afford a colorless powder (0.97 g, 62%).

Coevaporation with methylene chloride followed by extensive vacuum-drying at 40° C. removed traces of cyclohexane and afforded an analytical sample as an amorphous solid. Anal: Calc. [C(29)H(30)N(2)O(11)] C 59.79, H 5.19, N 4.81. Found: C 59.37, H 4.62, N 4.62, 0.93% water (K-F). NMR (DMSO-$d_6$): (Shows a 4:1 mixture of amide bond rotamers.) $\delta$ (major and minor) 1.034 (t, J=6.9 hz, 3H), 1.827 and 1.935 (m, 2H), 2.223

(m, 2H), 2.289 (s, 6H), 2.758 (s, 4H), 2.779 and 2.824 (s, 3H), 2.888 (q, J=6.8 hz, 2H), 4.333 and 4.473 (s, 2H), 7.043 (m, 4H), and 7.587 (per d, J=9.1 hz, 2H).

EXAMPLE 2

Preparation of a 512 nm fluorescent-labeled spacer-activated ester intermediate

A. Preparation of 4-Methylresorcinol 2,4-Dihydroxybenzaldehyde (33.97 gm, 0.246 mol) (recrystallized from toluene) was dissolved in spectroscopic grade 2-propanol (3 L) in a round bottom flask fitted with a gas inlet and a bubbler outlet. 10% Palladium on carbon (1.35 gm) was added followed by phosphoric acid (3 mL) and the mixture was sparged with nitrogen. The nitrogen flow was switched to hydrogen and the mixture was rapidly stirred with ice cooling. After 3 hours hydrogen uptake was complete and the catalyst was removed by filtration. The filtrate was stripped down to 200 mL and 200 mL of ethyl acetate was added. The solution was washed with 4×200 mL of water and the combined water extracts back-extracted with ethyl acetate. These organic extracts were water washed and the combined organic layers dried over sodium sulfate and stripped down to afford the product as a colorless crystalline solid (29.95 gm, 98%). M.p.: 106° C. (Lit. 106°–107° C. [J. C. Bell, W. Bridge, and A. Robertson, J. Chem. Soc., 1542–45 (1937)]). NMR (DMSO-$d_6$): $\delta$1.961 (s, Me), 6.076 (dd, H-6, J[5,6]=8 hz, J[2,6]=2 hz), 6.231 (d, H-2), 6.760 (d, H-5) 8.867 (s, OH), and 9.008 (s, OH).

B. Preparation of 9-Carboxyethylidene-3,6-dihydroxy-2,7-dimethyl-9H-xanthene (SF-512)

4-Methylresorcinol (25.8 g, 0.208 mol) and succinic anhydride (20.8 g, 0.208 g) were placed in a round bottom flask and the flask was purged with nitrogen. Methanesulfonic acid (150 mL) was added and the solution heated under nitrogen to 65° C. for 2 hours. The solution was added dropwise to 1 L of rapidly stirred, ice-cooled water with the simultaneous addition of 50% aq sodium hydroxide to maintain the pH at 2.25+/−0.25. The product was collected by centrifugation and washed with water (3×) and acetone (2×). The solid was air-dried, then vacuum-dried at 110° C. to afford a brick-red powder (24.1 g, 74%).

Purification was effected by allowing ethyl acetate to slowly diffuse into a solution of the product in dimethyl sulfoxide. The precipitate was collected by filtration, air-dried, then vacuum-dried. NMR (DMSO-$d_6$): (Shows pure delta form along with one mole each of water and dimethyl sulfoxide.) $\delta$2.124 (s, 6H), 3.421 (d, J=7.2 hz, 2H), 5.769 (t, J=7.2 hz, 1H); 6.512 (s, 1H), 6.573 (s, 1H); 7.295 (s, 2H), 9.681 (s, 1H), 9.825 (s, 1H), and 12.346 (bs, 1H). Vis. abs. (pH 8.2 aq Tris): max 493.5 nm.

C. Preparation of 9-Carboxyethyl-3,6-diacetoxy-2,7-dimethyl-9-ethoxy-9H-xanthene (Ac2EtSF-512)

A sample of SF-512 (20.0 g, 64.0 mmol) was added to acetic anhydride (350 mL) followed by pyridine (80 mL). This was stirred for 1 hour and then filtered to remove traces of unreacted dye. The filtrate was poured into 3.5 L of rapidly stirred water. The solid intermediate was collected by filtration, resuspended in 2 L cold water, stirred for 15 minutes, then recollected and air-dried to afford the spirolactone intermediate (20.8 g). This was dissolved in absolute ethanol (600 mL) and refluxed for 45 minutes. The solution was charcoal-treated and concentrated to 300 mL. The product was collected by filtration, rinsed with cold ethanol (2× 50 mL), air-dried, and then vacuum-dried to afford colorless microcrystals (14.9 g, 53%). M.p.: 143° C. Anal: Calc. [C(24)H(26)O(8)] C 65.15, H 5.92. Found: C 65.31, H 5.97. NMR (DMSO-$d_6$): $\delta$1.027 (t, J=6.9 hz, 3H), 1.628 (m, 2H), 2.136 (s, 6H), 2.207 (m, 2H), 2.303 (s, 6H), 2.884 (q, 6.9 hz, 2H), 6.939 (s, 2H), and 7.417 (s, 2H).

D. Preparation of 9-(2-(N-Succinimidyloxycarbonyl)ethyl)-3,6-diacetoxy-2,7-dimethyl-9-ethoxy-9H-xanthene (Ac2EtSF-512-NHS)

To a solution of Ac2EtSF-512 (9.42 g, 21.3 mmol) in methylene chloride (175 mL) was added N-hydroxysuccinimide (3.62 g, 31.5 mmol) followed immediately by 1-(3-dimethylaminopropyl)-3-ethylcarbodiimide hydrochloride (8.05 g, 42.0 mmol). The solution was stirred at room temperature for 2 hours. The mixture was washed with water (4×100 mL) and the aqueous washings back-extracted with methylene chloride (2×50 mL). The combined organic layers were dried over sodium sulfate and stripped down to an oil. Absolute ethanol was added and crystallization was induced by scratching. The product was collected by filtration, air-dried, then vacuum-dried to afford pale-orange microcrystals (9.80 g, 85%).

An analytical sample was prepared by dissolving 1 g in methylene chloride (10 mL) and adding cyclohexane (40 mL). Charcoal treatment followed by cooling and scratching induced crystallization affording a colorless crystalline solid. M.p.: 159° C. Anal: Calc. [C(28)H(29)N(1)O(10)] C 62.33, H 5.42, N 2.60. Found: C 62.06, H 5.71, N 2.39. NMR (DMSO-$d_6$): $\delta$1.053 (t, J=6.9 hz, 3H), 2.149 (s, 6H), 2.304 (s, 6H), 2.1–2.4 (m, 4H), 2.747 (s, 4H), 2.920 (q, J=6.9 hz, 2H), 6.975 (s, 2H), and 7.464 (s, 2H).

E. Preparation of 9-(2-(N-methyl-N-(benzyloxycarbonylmethyl)carboxamido)ethyl)-3,6-diacetoxy-2,7-dimethyl-9-ethoxy-9H-xanthene (Ac2EtSF-512-Sar-OBn)

To a solution of sarcosine benzyl ester (0.72 g, 4.02 mmol) in methylene chloride (25 mL) was added Ac2EtSF-512-NHS (1.73 g, 3.21 mmol) and 5% aq sodium bicarbonate solution (20 mL). The two-phase mixture was stirred rapidly for 20 hours. The layers were separated and the organic layer washed with 3×15 mL water, dried over sodium sulfate, and concentrated to 10 mL. The solution was diluted to 60 mL with cyclohexane, charcoal-treated, and reduced to 25 mL under a stream of nitrogen resulting in the precipitation of the product. The supernatant was decanted and the colorless solid vacuum-dried (1.44 g, 74%).

Recrystallization from methylene chloride/cyclohexane with charcoal treatment afforded an analytical sample. M.p.: 150°–2° C. Anal: Calc. [C(34)H(37)N(1)O(9)] C 67.65 H 6.18 N 2.32. Found: C 67.42 H 6.08 N 2.33. NMR (DMSO-$d_6$): (Shows 5:2 mixture of amide bond rotamers.) $\delta$ (major and minor) 1.049 and 1.008 (t, J=6.8 hz, 3H), 1.747 and 1.66 (m, 2H), 2.144 and 2.115 (s, 6H), 2.18 (m, 2H), 2.314 and 2.303 (s, 6H), 2.694 (s, 3H), 2.907 and 2.884 (q, J=6.8 hz, 2H), 3.961 (s, 2H), 5.075 and 5.016 (s, 2H), 6.960 and 6.917 (s, 2H), 7.430 and 7.396 (s, 2H), and 7.30 (m, 5H).

F. Preparation of 9-(2-(N-Methyl-N-(N'-succinimidyloxycarbonylmethyl)carboxamido)ethyl)-3,6-diacetoxy-9-ethoxy-2,4,5,7-tetramethyl-9H-xanthene (Ac2EtSF-512-Sar-NHS)

To a suspension of Ac2EtSF-512-Sar-OBn (0.45 g, 0.745 mol) in absolute ethanol (20 mL) was added 10% palladium on carbon (0.05 g). The mixture was stirred under balloon pressure of hydrogen for 30 minutes. The catalyst was removed by filtration and the ethanol stripped off to afford a syrupy residue.

This residue was dissolved in methylene chloride (25 mL) and N-hydroxysuccinimide (0.129 g, 1.12 mmol) and 1-(3-dimethylaminopropyl)-3-ethylcarbodiimide hydrochloride (0.292 g, 1.52 mmol) were added. The mixture was stirred for 30 minutes and then washed with water (3×15 mL). The solution was dried over sodium sulfate, concentrated to 10 mL, diluted to 40 mL with cyclohexane, charcoal treated, and reduced in volume to 20 mL under a stream of nitrogen. The supernatant was decanted and the residue subjected to a second precipitation from methylene chloride to afford a colorless powder (0.27 g, 59%). Anal: Calc. [C(31)H(34)N(2)O(11)] C 60.98, H 5.61, N 4.59. Found: C 60.28, H 5.71, N 4.40, 1.08% water (K-F). NMR (DMSO-d$_6$): (Shows a 5:1 mixture of rotamers about the amide bond.) $\delta$ (major and minor) 1.043 (t, J=7.0 hz, 3H), 1.793 and 1.933 (m, 2H), 2.145 and 2.133 (s, 6H), 2.198 (m, 2H), 2.314 (s, 6H), 2.740 (s, 4H), 2.778 and 2.821 (s, 3H), 2.900 (q, J=7.0 hz, 2H), 4.334 and 4.469 (s, 2H), 6.960 and 6.925 (s, 2HO, and 7.441 (s, 2H).

EXAMPLE 3

Preparation of a 519 nm fluorescent-labeled spacer-activated ester intermediate

A. Preparation of 9-(2-Carboxyethylidene)-3,6-dihydroxy-4,5-dimethyl-9H-xanthene (SF-519)

2-Methylresorcinol (37.2 g, 0.300 mol) and succinic anhydride (30.0 g, 0.300 mol) were placed in a round bottomed flask and purged with nitrogen. Methanesulfonic acid (150 mL) was added and the solution was stirred at 65° C. for 4 hours under an atmosphere of nitrogen. The reaction mixture was added dropwise to rapidly stirred, ice-cooled water (1 L) with simultaneous addition of 50% aqueous sodium hydroxide to maintain pH 6.0+/−0.5. The finely divided solid was collected by centrifugation and rinsed with water (4×250 mL), each time resuspending, spinning down, and discarding the supernatant. The crude product was suspended in water (1 L) and sufficient aqueous sodium hydroxide (50%) was added to raise the pH to 10.2. The solution was filtered and the filtrate brought to pH 1.2 with concentrated HCl. The product was collected by centrifugation and rinsed with water (3×350 mL) and acetone (3×250 mL) as described above. The resulting solid was azeotroped with toluene, collected by filtration, and vacuum-dried at 110° C. to afford a brick-red powder (24.6 g, 53%). Anal: Calc. [C(18)H(16)O(5)] C 69.22 H 5.16. Found: C 68.95 H 5.30, 0.80% water (K-F). NMR (DMSO-d$_6$) (mostly delta form): $\delta$2.164 (s, 3H), 2.177 (s, 3H), 3.376 (d, J=7.1 hz, 2H), 5.749 (t, J=7.2 hz, 1H), 6.642 (d, J=8.8 hz, 1H), 6.672 (d, J=8.8 hz, 1H), 7.216 (d, J=8.5 hz, 1H), 7.227 (d, J=8.5 hz, 1H), 9.602 (bs, 1H), and 9.758 (bs, 1H). Vis. abs. (pH 8.2; 50 mM aq Tris/HCl) max 500 nm (69,800).

B. Preparation of 9-(2-Carboxyethyl)-3,6-diacetoxy-4,5-dimethyl-9-ethoxy-9H-xanthene (Ac2EtSF-519)

SF-519 (15.0 g, 48.0 mmol) was added to acetic anhydride (250 mL) and the solid was pulverized. (Sonication is useful to disperse the highly insoluble SF-519.) The suspension was ice-cooled, pyridine (50 mL) was added, and the mixture stirred for 20 minutes. The solution was filtered and added in a slow but steady stream to rapidly stirred ice-cold water (4 L). After stirring for an additional 20 minutes, the intermediate product was filtered, resuspended in water (3 L), and stirred for another 25 minutes. The solid was collected by filtration and air-dried. The dried intermediate was dissolved in absolute ethanol (600 mL) and refluxed for 1 hour. The solution was concentrated on a rotary evaporator to 200 mL which resulted in crystallization. The product was collected by filtration, air-dried, then vacuum-dried to afford colorless microcrystals (12.13 g, 57%).

An analytical sample was prepared by precipitation from methylene chloride solution with cyclohexane. NMR (DMSO-d$_6$): $\delta$1.033 (t, J=6.9 hz, 3H), 1.674 (m, 2H), 2.189 (s, 6H), 2.19 (m, 2H), 2.348 (s, 6H), 2.878 (q, J=6.9 hz, 2H), 7.006 (d, J=8.6 hz, 2H), and 7.399 (d, J=8.6 hz, 2H).

C. Preparation of 9-(2-(N-Succinimidyloxycarbonyl)ethyl-3,6-diacetoxy-4,5-dimethyl-9-ethoxy-9H-xanthene (Ac2EtSF-519-NHS)

Ac2EtSF-519 (7.80 g, 17.6 mmol) was mixed with methylene chloride (175 mL) and N-hydroxysuccinimide (2.75 g, 23.9 mmol) and 1-(3-dimethylaminopropyl)-3-ethylcarbodiimide hydrochloride (7.00 g, 36.5 mmol) were added. The mixture was stirred for 90 minutes and then washed with water (5×100 mL). The combined aqueous layers were back extracted with methylene chloride (2×50 mL) and the pooled organic layers were dried over sodium sulfate and stripped down. Trituration with ethanol (100 mL) followed by filtration and air-drying afforded the product as a light yellow solid (7.45 g, 78%).

Two recrystallizations from cyclohexane/methylene chloride with charcoal treatment afforded an analytical sample. M.p.: 164°–5° C. Anal: Calc. [C(28)H(29)N(1)O(10)] C 62.33, H 5.42, N 2.60. Found: C 62.17, H 5.47, N 2.48. NMR (DMSO-d$_6$): $\delta$1.051 (t, J=7.0 hz, 3H), 2.4–2.1 (m, 4H), 2.191 (s, 6H), 2.337 (s, 6H), 2.715 (s, 4H), 2.912 (q, J=7.0 hz, 2H), 7.015 (d, J=8.6 hz, 2H), and 7.429 (d, J=8.6 hz, 2H).

D. Preparation of 9-(2-(N-methyl-N-(benzyloxycarbonylmethyl)carboxamido)ethyl)-3,6-diacetoxy-4,5-dimethyl-9-ethoxy-9H-xanthene (Ac2EtSF-519-Sar-OBn)

To a solution of sarcosine benzyl ester (0.557 g, 3.11 mmol) in methylene chloride (19 mL) was added Ac2EtSF-519-NHS (1.30 g, 2.41 mmol) and 5% aqueous sodium bicarbonate solution (15 mL). The two-phase mixture was stirred rapidly for 18 hours. The layers were separated and the organic layer washed with 3×10 mL water, dried over sodium sulfate, and concentrated to 10 mL. The solution was diluted to 40 mL with cyclohexane, charcoal-treated, and reduced to 20 mL under a stream of nitrogen resulting in the precipitation of the product as a sticky solid. The supernatant was decanted away and the residue coevaporated with methylene chloride to afford a colorless foam (0.97 g, 67%).

Extensive vacuum drying afforded an analytical sample. Anal: Calc. [C(34)H(37)N(1)O(9)] C 67.65 H 6.18 N 2.32. Found: C 67.43 H 6.37 N 2.32. NMR (DMSO-d$_6$) (Shows 5:2 mixture of amide bond rotamers.): δ(major and minor) 1.044 and 1.020 (t, J=7.0 hz, 3H), 1.824 and 1.714 (m, 2H), 2.17 (m, 2H), 2.195 and 2.169 (s, 6H), 2.346 and 2.337 (s, 6H), 2.720 and 2.691 (s, 3H), 2.889 (q, J=7.0 hz, 2H), 3.959 and 3.988 (s, 2H), 5.073 and 5.048 (s, 2H), 7.000 and 6.954 (d, J=8.6 hz, 2H), and 7.45–7.25 (m, 7H).

E. Preparation of 9-(2-(N-Methyl-N-(N'-succinimidyloxycarbonylmethyl)carboxamido)ethyl)-3,6-diacetoxy-4,5-dimethyl-9-ethoxy-9H-xanthene (Ac2EtSF-519-Sar-NHS)

To a solution of Ac2EtSF-519-Sar-OBn (1.35 g, 2.24 mmol) in absolute ethanol (50 mL) was added 10% palladium on carbon (0.13 g). The mixture was stirred under balloon pressure of hydrogen for 20 minutes. The catalyst was removed by filtration and the ethanol stripped off to afford a syrupy residue.

This residue was dissolved in methylene chloride (50 mL) and N-hydroxysuccinimide (0.39 g, 3.39 mmol) and 1-(3-dimethylaminopropyl)-3-ethylcarbodiimide hydrochloride (1.57 g, 8.19 mmol) were added. The mixture was stirred for 75 minutes and then washed with water (4×15 mL). The solution was dried over sodium sulfate, concentrated to 25 mL, diluted to 125 mL with cyclohexane, charcoal treated, and reduced in volume to 50 mL under a stream of nitrogen. The supernatant was decanted and the remaining oil taken up in methylene chloride (5 mL) and added dropwise to rapidly stirred cyclohexane (75 mL) to afford a colorless powder (0.587 g, 43%).

To provide an analytical sample a portion of the product was taken up in methylene chloride, dried over molecular sieves, evaporated under a stream of nitrogen, and finally dried in a drying pistol at 48° C. over phosphorus pentoxide for 20 hours. Anal: Calc. [C(31)H(34)N(2)O(11)]; C 60.98, H 5.61, N 4.59. Found: C 60.15, H 5.71, N 4.51, water (K-F) 1.51%. NMR (DMSO-d$_6$) (Shows a 4:1 mixture of amide bond rotamers.): δ(major and minor) 1.039 (t, J=6.9 hz, 3H), 1.841 and 1.945 (m, 2H), 2.19 (m, 2H), 2.194 (s, 6H), 2.345 (s, 6H), 2.767 and 2.744 (s, 4H), 2.778 and 2.825 (s, 3H), 2.888 (q, J=6.9 hz, 2H), 4.328 and 4.461 (s, 2H), 7.000 (d, J=8.6 hz, 2H), and 7.410 (d, J=8.6 hz, 2H).

EXAMPLE 4

Preparation of a 526 nm fluorescent-labeled spacer-activated ester intermediate

A. Preparation of 2,4-Dihydroxy-3-methylbenzaldehyde

Phosphorus oxychloride (80 mL, 0.86 mol) was added to a stirred mixture of N-methylformanilide (102 mL, 0.82 mol) in ether (250 mL). The mixture was stirred for 1 hour at room temperature and then cooled in ice. 2-Methyl resorcinol (Aldrich, 100 g, 0.81 mol) was added and the mixture was allowed to warm to room temperature while stirring overnight. The precipitated intermediate product was collected by filtration and rinsed with ether (3×). The intermediate was hydrolyzed by dissolving in a mixture of acetone (250 mL) and water (250 mL) and stirring for 30 minutes. Water (2 L) was added, the mixture was brought to a boil, and then allowed to cool and deposit crystalline product. This was recrystallized a second time from water (4 L) to afford pure product (70 g, 57%). M.p. 150° C. (Lit. 152°–3° C. [W. Baker et al., *J. Chem. Soc.*, 2834–5 (1949).]. NMR (DMSO-d$_6$): δ1.973 (s, 3H), 6.551 (d, J=8.5 hz, 1H), 7.428 (d, J=8.5 hz, 1H), 9.703 (s, 1H), 10.745 (s, 1H), and 11.592 (s, 1H).

B. Preparation of 2,4-dimethylresorcinol

A solution of 2,4-dihydroxy-3-methylbenzaldehyde (30.0 g, 197 mmol) with isopropanol (3 L) was ice-cooled in a 5 L 3-neck flask fitted with a magnetic stirrer. Phosphoric acid (4 mL) and 10% palladium on carbon were added and the solution was sparged with nitrogen, then hydrogen. When uptake was judged to be complete (c. 1.5 hour) the solution was again sparged with nitrogen and then filtered through Celite ®. The solvent was stripped off, the residue taken up in ethyl acetate, and the resulting solution washed with water (4×100 mL). The water washes were back-extracted with ethyl acetate and the combined organic layers dried over sodium sulfate and stripped down. Sublimation (95°, 0.05 torr) afforded a colorless solid (19.6 g, 72%). M.p. 107°–8° C. (Lit. 108°–109° C. [W. Baker et al., *J. Chem. Soc.*, 2834–5 (1949).]). NMR (DMSO-d$_6$): δ1.969 (s, 3H), 2.037 (s, 3H), 6.220 (d, J=8.1 hz, 1H), 6.637 (d, J=8.1 hz, 1H), 7.929 (s, 1H), and 8.785 (s, 1H).

C. Preparation of 9-(2-Carboxyethylidene)-3,6-dihydroxy-2,4,5,7-tetramethyl-9H-xanthene (SF-526)

2,4-Dimethylresorcinol (28.4 g, 0.205 mol) and succinic anhydride (20.0 g, 0.200 mol) were placed in a round bottomed flask and purged with nitrogen. Methanesulfonic acid (231 mL) was added and the solution was stirred at 70° C. for 20 hours under an atmosphere of nitrogen. The reaction mixture was added dropwise to a rapidly stirred mixture of aqueous sodium hydroxide (95 g in 150 mL water) and ice (3 L). Sufficient methanesulfonic acid was added to bring the final pH from 4.7 to 1.5. The resulting solid was collected by centrifugation and washed by suspending, spinning down, and decanting from water (5×1.2 L). The final suspension was collected by filtration, air-dried, then oven-dried at 110° C. for 6 hours to afford a brick-red solid (30.6 g, 44%).

A second precipitation from alkaline solution, followed by centrifugation and water washes afforded an analytical sample. Anal: Calc. [C(16)H(12)O(5)] C 70.57, H 5.92. Found: C 70.39, H 6.00, 0.21% water (K-F). NMR (DMSO-d$_6$) (mostly spirolactone form): δ2.172 (s, 12H), 2.508 (m, 2H), 3.342 (m, 2H), and 7.604 (s, 2H). Vis. abs. (pH 8.2; 50 mM aq Tris/HCl): 509 nm (71,300).

D. Preparation of 9-(2-Carboxyethyl)-3,6-diacetoxy-9-ethoxy-2,4,5,7-tetramethyl-9H-xanthene (Ac2EtSF-526)

SF-526 (25.2 g, 74 mmol) was added to ice-cold acetic anhydride (450 mL) followed by pyridine (100 mL) and the mixture was stirred with ice-cooling for 150 minutes. The reaction mixture was filtered then added in a slow, steady stream to rapidly stirred, ice-cold water (7 L). After stirring for an additional 30 minutes, the intermediate product was filtered, washed with water, resuspended in water (4 L) and stirred for another 30 minutes. The solid was collected by filtration and air-dried to afford the spirolactone intermediate (28.9 g). A portion of this intermediate (18.6 g) was dissolved in absolute ethanol (1 L), and refluxed for 90 minutes. The solution was concentrated on a rotary evaporator to 300 mL which resulted in crystallization. The product was collected by filtration, rinsed with ethanol, air-dried, then vacuum-dried to afford colorless microcrystals (11.6 g, 52% based on amount of intermediate used).

Recrystallization from methylene chloride/cyclohexane with charcoal treatment gave colorless microcrystals. M.p.: 154°–155° C. Two evaporations from methylene chloride removed traces of cyclohexane for analysis. Anal: Calc. [C(20)H(20)O(5)] C 70.57, H 5.92. Found: C 70.39, H 6.00, 0.21% water (K-F). NMR (DMSO-$d_6$) (mostly spirolactone form): δ2.172 (s, 12H), 2.508 (m, 2H), 3.342 (m, 2H), and 7.604 (s, 2H). Vis. abs. (pH 8.2; 50 mM aq Tris/HCl): 509 nm (71,300).

E. Preparation of 9-(2-(N-Succinimidyloxycarbonyl)ethyl)-3,6-diacetoxy-9-ethoxy-2,4,5,7-tetramethyl-9H-xanthene (Ac2EtSF-526-NHS)

Ac2EtSF-526 (4.70 g, 9.99 mmol) was mixed with methylene chloride (75 mL) and 1-(3-dimethylaminopropyl)-3-ethylcarbodiimide hydrochloride (3.10 g, 16.2 mmol) and N-hydroxysuccinimide (1.50 g, 13.0 mmol) were added. The mixture was stirred for 90 minutes and then washed with water (4×50 mL). The combined aqueous layers were back extracted with methylene chloride (50 mL) and the pooled organic layers were dried over sodium sulfate and stripped down. Trituration with ethanol (75 mL) followed by filtration and air-drying afforded the crude product as a light yellow solid (c. 4.7 g). This material was dissolved in methylene chloride (50 mL) and cyclohexane (50 mL) was added. One teaspoon of charcoal was added, the mixture was filtered, and the product was brought down with an additional portion of cyclohexane (25 mL). Collection by filtration, air-drying, and vacuum-drying afforded colorless crystals (3.14 g, 55%).

A second precipitation from methylene chloride with cyclohexane afforded an analytical sample. Anal: Calc. [C(30)H(33)N(1)O(10)]; C 63.48, H 5.86, N 2.47. Found: C 63.08, H 6.00, N 2.37. NMR (DMSO-$d_6$): δ1.058 (t, J=6.9 hz, 3H), 2.136 (s, 6H), 2.155 (s, 6H), 2.228 (m, 4H), 2.371 (s, 6H), 2.748 (s, 4H), 2.918 (q, J=6.9 hz, 2H), and 7.300 (s, 2H).

F. Preparation of 9-(2-(N-methyl-N-(benzyloxycarbonylmethyl)carboxamido)ethyl)-3,6-diacetoxy-9-ethoxy-9H-xanthene (Ac2EtSF-505-Sar-OBn)

To a solution of sarcosine benzyl ester (0.72 g, 4.02 mmol) in methylene chloride (40 mL) was added Ac2EtSF-526-NHS (1.82 g, 3.21 mmol) and 5% aq sodium bicarbonate solution (30 mL). The two-phase mixture was stirred rapidly for 20 hours. The layers were separated and the organic layer washed with 4×15 mL water, dried over sodium sulfate, and concentrated to 15 mL. The solution was diluted to 100 mL with cyclohexane, charcoal-treated, and reduced to 50 mL under a stream of nitrogen resulting in the precipitation of the product. Filtration followed by air-drying afforded a colorless solid (0.96 g, 47%).

Coevaporation with methylene chloride followed by extensive vacuum drying afforded an analytical sample. Anal: Calc. for [C(36)H(41)N(1)O(9)] C 68.45, H 6.54, N 2.22. Found: C 68.29, H 6.70, N 2.07. NMR (DMSO-$d_6$) (Shows 5:2 mixture of amide bond rotamers.): δ(major and minor) 1.049 and 1.027 (t, J=6.8 hz, 3H), 1.783 and 1.700 (m, 2H), 2.129 and 2.099 (s, 6H), 2.159 and 2.129 (s, 6H), 2.14 (m, 2H), 2.379 and 2.371 (s, 6H), 2.699 and 2.690 (s, 3H), 2.873 (q, J=6.8 hz, 2H), 3.958 and 3.976 (s, 2H), 5.075 and 5.019 (s, 2H), 7.266 and 7.233 (s, 2H), and 7.25–7.40 (m, 5H).

G. Preparation of 9-(2-(N-Methyl-N-(N'-succinimidyloxycarbonylmethyl)carboxamido)ethyl)-3,6-diacetoxy-9-ethoxy-2,4,5,7-tetramethyl-9H-xanthene (Ac2EtSF-526-Sar-NHS)

To a solution of Ac2EtSF-526-Sar-OBn (0.96 g, 1.52 mmol) in absolute ethanol (40 mL) was added 10% palladium on carbon (0.10 g). The mixture was stirred under balloon pressure of hydrogen for 30 minutes. The catalyst was removed by filtration and the ethanol stripped off to afford a syrupy residue.

This residue was dissolved in methylene chloride (40 mL) and N-hydroxysuccinimide (0.26 g, 2.26 mmol) and 1-(3-dimethylaminopropyl)-3-ethylcarbodiimide hydrochloride (0.59 g, 3.08 mmol) were added. The mixture was stirred for 30 minutes and then washed with water (4×15 mL). The solution was dried over sodium sulfate, concentrated to 15 mL, diluted to 100 mL with cyclohexane, charcoal treated, and reduced in volume to 50 mL under a stream of nitrogen. The product was collected by filtration, air dried, and vacuum dried to afford colorless microcrystals (0.573 g, 59%).

Coevaporation with methylene chloride followed by extensive vacuum drying at 40° C. removed traces of cyclohexane and afforded an analytical sample as an amorphous solid. NMR (DMSO-$d_6$): δ1.043 (t, J=6.7 hz, 3H), 1.82 (m, 2H), 2.130 (s, 6H), 2.157 (s, 6H), 2.15 (m, 2H), 2.378 (s, 6H), 2.748 (s, 4H), 2.778 (s, 3H), 2.891 (q, J=6.7 hz, 2H), 4.327 (s, 2H), and 7.275 (s, 2H).

EXAMPLE 5

PREPARATION OF 5-(3-AMINO-1-PROPYNYL)-2',3'-DIDEOXYCYTIDINE 5'-TRIPHOSPHATE (5-AP3-ddCTP)

A. PREPARATION OF N-PROPARGYLTRIFLUOROACETAMIDE (18)

Propargylamine (24.79 g, 0.450 mole; Aldrich, 99%) was added dropwise over 1 hour to methyl trifluoroacetate (69.19 g, 0.540 mole, 1.2 eq, Aldrich) at 0°. After stirring an additional hour at 0°, distillation through a 15 cm Vigreaux column afforded 62.12 g (91%) of trifluoroacetamide 18 as a colorless liquid (bp 68.5°–69.5° at 11 torr). This material was homogeneous by NMR and GC and was used interchangeably with spectroscopically-identical material prepared by acylating propargylamine with trifluoroacetic acid anhydride.

$^1$H-NMR (CDCl$_3$): 6.85 (broad s, 1H, NHTFA), 4.17 (dd, J=5.6 and 2.5, 2H, CH$_2$), 2.35 (t, J=2.5, 1H, CH). IR (neat; cm$^{-1}$): 3300 (N-H), 3095 and 2935 (C-H), 2130 (acetylene), 1720 (C=O), 1550 (N-H), 1430, 1365, 1160, 1040, 998, 918, 857, 829, 772, and 725.

B. PREPARATION OF 5-IODO-2',3'-DIDEOXYCYTIDINE (19)

A solution of 2',3'-dideoxycytidine (2.11 g, 10 mmol, Raylo) and mercuric acetate (3.35 g, 10.5 mmol, Fisher) in 50 mL of methanol was refluxed for 19 hours. The resulting white suspension was diluted with methanol (50 mL) and dichloromethane (100 mL). Iodine (3.05 g, 12 mmol) was added and the suspension was stirred at 25°. After 4 hours, the free base form of AG3 X4A resin (20 mL, 38 meq, Bio-Rad) was added and hydrogen sulfide was bubbled into the reaction for 15 minutes. Complete precipitation of mercury(II) was verified by TLC. The reaction was filtered through filter aid and the filter aid was washed with 1:1 methanol-dichloromethane. The filtrate was evaporated onto silica gel (10 g) and the loaded silica gel was placed on top of a 150 g silica gel column. Elution with 5%, 10% and 20% methanol in dichloromethane afforded 2.79 g (83%) of iodide 19 as a colorless crystalline solid. Two recrystallizations from boiling water afforded, after vacuum-drying at 50°, large, analytically-pure prisms (mp: d 178°).

$^1$H-NMR (DMSO-d$_6$): 8.50 (s, 1H, H6), 7.73 (broad s, 1H, —NH$_2$a), 6.53 (broad s, 1H, —NH$_2$b), 5.86 (dd, J=6.5 and 2.1, 1H, H1'), 5.19 (t, 1H, 5'OH), 4.04 (m, 1H, H4'), 3.75 (ddd, J=12.1, 5.2, and 2.9, 1H, H5'a), 3.53 (dt, J=12.1 and 3.8, 1H, H5'b), and 2.3–1.7 (m, 4H, H2' and H3'). Calculated for C$_9$H$_{12}$N$_3$O$_3$I: C 32.07%, H 3.59%, N 12.46%. Found: C 32.05%, H 3.80%, N 12.46%.

C. PREPARATION OF 5-(3-TRIFLUOROACETAMIDO-1-PROPYNYL)-2',3'-DIDEOXYCYTIDINE (20): A GENERAL PROCEDURE FOR COUPLING AMINOALKYNES TO IODONUCLEOSIDES

A 50-mL, three-necked flask was charged with iodocytidine 19 (770 mg, 2.00 mmol) and cuprous iodide (76.2 mg, 0.400 mmol, 0.20 eq; Aldrich, Gold Label). After flushing the flask with argon, dry dimethylformamide (10 mL, Aldrich) was added to produce a 0.2M solution of iodocytidine which contained suspended cuprous iodide. N-Propargyltrifluoroacetamide (0.70 mL, 6.00 mmol, 3.0 eq) and triethylamine (0.56 mL, 4.00 mmol, 2.0 eq, stored over molecular sieves) were added via syringe. Tetrakis(triphenylphosphine)palladium(0) (231 mg, 0.20 mmol, 0.10 eq) was weighed into a vial in a dry box and added to the reaction mixture. The cuprous iodide dissolved, affording a yellow solution which gradually darkened over several hours. The reaction was allowed to proceed until TLC indicated that the starting material was completely consumed. After 4 hours, the reaction was diluted with 20 mL of 1:1 methanol-dichloromethane and the bicarbonate form of a strongly basic anion exchange resin (Bio-Rad AG1 X8, 2.0 g, ca. 6 eq) was added. After stirring for about 15 minutes, evolution of gas ceased. After 30 minutes, the reaction mixture was filtered and the resin was washed with 1:1 dichloromethane-methanol. The combined filtrates were rapidly concentrated with a rotary evaporator. (Removal of dimethylformamide required about 10 minutes at 45° and 2 torr.) The residue was immediately purified by chromatography on 150 g of silica gel using 10%, 15% and 20% methanol in dichloromethane. Removal of solvent from the appropriate fractions afforded 651 mg (90%) of alkynylamine 20 as a pale yellow crystalline foam which was homogeneous by TLC and NMR. The product from a similar preparation was established to be a hemi-hydrate by elemental analysis.

$^1$H-NMR (DMSO-d$_6$): 9.96 (broad s, 1H, NHTFA), 8.32 (s, 1H, H6), 7.76 (broad s, 1H, NH$_2$a), 6.78 (broad s, 1H, NH$_2$b), 5.88 (dd, J=6.5 and 2.5, 1H, H1'), 5.13 (t, J=5.1, 1H, 5'OH), 4.28 (d, J=5.0, 2H, —CH$_2$—), 4.04 (m, 1H, H4'), 3.73 (ddd, J=12.0, 5.0 and 3.1, 1H, H5'a), 3.53 (dt, J=12.1 and 4.0, 1H, H5'b), 2.3–1.7 (m, 4H, H2' and H3'). $^{19}$F-NMR (DMSO-d$_6$): —74.0 (s). UV (MeOH): maxima at 238.5 (17,100) and 295.5 (9,300). Calculated for C$_{14}$H$_{15}$N$_4$O$_4$F$_3$·½H$_2$O: C 45.53, H 4.37, N 15.17. Found: C 45.56, H 4.52, N 15.26.

D. PREPARATION OF TRIS(TRI-N-BUTYLAMMONIUM)PYROPHOSPHATE

Tetrasodium pyrophosphate decahydrate (4.46 g, 10 mmol) was dissolved in the minimum amount of water (about 50 mL) and passed through a column of AG50W X8 resin (100–200 mesh, 4×10 cm bed) poured in water. The column was eluted with water and the eluent was collected in an ice-cooled flask until pH of the eluent approached neutrality. Tri-n-butylamine (Aldrich Gold Label, 7.1 mL, 30 mmol) was added to the eluent and the two phases were stirred vigorously until all of the amine dissolved. The resulting solution was lyophilized. The residue was co-evaporated twice with dry pyridine and once with dry dimethylformamide. The residue was dissolved in dry dimethylformamide (10 mL) and the resulting 1.0M solution was stored (for as long as one month) at 0° under argon until used.

E. PREPARATION OF 5-(3-AMINO-1-PROPYNYL)-2',3'-DIDEOXYCYTIDINE 5'-TRIPHOSPHATE (5-AP3-ddCTP). A GENERAL PROCEDURE FOR CONVERTING PROTECTED ALKYLNYLAMINO NUCLEOSIDES TO THE CORRESPONDING 5'-TRIPHOSPHATES AND REMOVING THE TRIFLUOROACETYL PROTECTING GROUP

Alkynylamino nucleoside 20 (361 mg, 1.00 mmol) was dissolved in trimethyl phosphate (2.0 mL, Aldrich Gold Label) while stirring under argon in an oven-dried flask. The solution was cooled to −10° and phosphorus oxychloride (0.093 mL, 1.00 mmol, Aldrich Gold Label) was added by syringe. After stirring the reaction mixture at −10° for 30 minutes, a second aliquot of phosphorus oxychloride (0.093 mL, 1.00 mmol) was added and the solution was allowed to warm slowly to 25° while stirring. Aliquots from the reaction mixture were quenched with 1N aqueous hydroxide and analyzed by HPLC. When conversion to the corresponding nucleotide monophosphate was at a maximum (in this case 100 minutes after the second addition of phosphorus oxychloride), the reaction mixture was added dropwise to a precooled (−10°) solution of tris(tri-n-butylammonium)pyrophosphate (6.0 mL of the above 1.0M solution in dry dimethylformamide). The solution was allowed to warm slowly to 25° while stirring under argon. After 100 minutes, the reaction solution was added slowly to a precooled (0°) solution of triethylamine (1.4 mL) in water (20 mL). The solution was stirred with ice-cooling for 15 minutes and then allowed to stand overnight at about 2°.

The volatiles were removed by vacuum evaporation at 25° and 0.5 torr. The residue was redissolved in water (75 mL) and applied to a column of DEAE-Sephadex A-25-120 (2.6×65 cm bed) that had been equilibrated with: 1) pH 7.6, 1.0M aqueous TEAB (300 mL), 2) 1.0M aqueous potassium bicarbonate (300 mL), and 3) pH 7.6, 0.1M aqueous TEAB (300 mL). The column was eluted with a linear gradient of pH 7.6 aqueous TEAB from 0.1M (1 L) to 1.0M (1 L). The column was driven at 100 mL/h while collecting fractions every 12 minutes. The elution was monitored by absorbance at 270 nm (40

AUFS). The desired material eluted as a well-separated, major band near the end of the gradient (Fractions 73–80). The product-containing fractions were pooled, concentrated (at below 30°), and co-evaporated twice with absolute ethanol. The residue was taken up in water (20.4 mL) and lyophilized.

The intermediate product was taken up in water (12.5 mL) and concentrated ammonium hydroxide (12.5 mL) was added. After stirring for 3.5 hours, the solution was stirred under aspirator vacuum for 2 hours to remove the excess ammonia gas and then lyophilized. The residue was taken up in pH 7.6 0.1M aqueous TEAB (10 mL) and applied to a column of DEAE-Sephadex A-25-120 (1.6×55 cm bed) that had been prepared as described above. The column was eluted while collecting 6 mL fractions with a linear gradient of TEAB from 0.1M (280 mL) to 1.0M (280 mL). The product eluted as a single major peak. The fractions estimated to contain pure product (#39–45) were pooled, concentrated (at below 30°), co-evaporated with absolute ethanol (2×), and taken up in water (9.8 mL). The solution was assayed by UV absorption and HPLC and then lyophilized.

A dilute solution of the product showed absorption maxima at 240 and 293.5 nm in pH 8.2 50 mM aqueous Tris buffer. Assuming an absorption coefficient for the product equal to that of the starting material (9,300), the yield of 5-AP3-ddCTP, based on the absorption at 293.5 nm, was 0.32 mmol (32%). HPLC (Zorbax SAX, 0.2M pH 6.5 aqueous potassium phosphate, monitoring 270 nm) of the final product showed essentially a single peak (>99%).

$^1$H-NMR (D$_2$O): 8.57 (s, 1H, H6), 6.03 (dd, J=6.4 and 1.6, 1H, H1'), 4.42 (m, 2H, H4' and H5'a), 4.18 (ddd, J=12, 5.5 and 3, 1H, H5'b), 4.036 (s, 2H, —CH$_2$—), 2.5–1.9 (m, 4H, H2' and H3'), plus counterion (triethylammonium) peaks. $^{31}$P-NMR (D$_2$O): −9.02 (d, J=20, 1P), −9.74 (d, J=20, 1P), −21.37 (t, J=20, 1P). UV (pH 8.2 aq Tris): maxima at 240 and 293.5 nm.

EXAMPLE 6
PREPARATION OF 5-(3-AMINO-1-PROPYNYL)-2',3'-DIDEOXYURIDINE 5'-TRIPHOSPHATE (5-AP3-ddUTP)

A. PREPARATION OF 5-IODO-2',3'-DIDEOXYURIDINE (21)

Dideoxyuridine (2.122 g, 10.0 mmol) was dissolved in 30 mL of warm methanol and, after cooling to 25°, iodine monochloride (4.06 g, 25 mmol, 2.5 eq, Fisher) in methanol (20 mL) was added over 5 minutes. The dark purple reaction mixture was heated in a 50° bath under nitrogen for 20 minutes and then immediately cooled in an ice-water bath. After standing without stirring for 165 minutes, the resulting precipitate was collected by filtration and washed with cold methanol (2×10 mL). Vacuum-drying overnight afforded 2.232 g (66%) of iodide 21 as off-white microcrystals. This material was used without further purification in the next reaction, but other preparations were purified by chromatography or recrystallization from boiling methanol (30 mL/g) to give white needles (mp d 160°–164°). NMR indicated that the crude precipitate was homogeneous, but also that the 5'-hydroxyl proton was very broad due to exchange catalyzed by trace impurities. Chromatographed or recrystallized materials afforded spectra in which this proton was, as usual, a sharp triplet.

$^1$H-NMR (DMSO-d$_6$): 11.60 (broad s, 1H, H3), 8.57 (s, 1H, H6), 5.90 (dd, J=2.0 and, 6.6, 1H, H1'), 5.2 (broad s, 1H, 5'OH), 4.06 (m, 1H, H4'), 3.75, and 3.53 (m, 1H, H5'), 2.26, 2.02 and 1.84 (m, 4H, H2' and H3').

B. PREPARATION OF 5-(3-TRIFLUOROACETAMIDO-1-PROPYNYL)-2',3'-DIDEOXYURIDINE (22)

Iodouridine 21 was coupled for 3 hours to N-propargyltrifluoroacetamide following the general method given in Example 5C. Chromatography with a 0–5% methanol in dichloromethane gradient afforded material which was homogeneous by TLC, but which was difficult to dry. After co-evaporating the chromatographed product several times with chloroform and vacuum-drying, 536.5 mg of alkynylamino nucleoside 22 was obtained as a white foam. This material was homogeneous by TLC and was pure by NMR except for a small amount (39 mole %; corrected yield 66%) of chloroform.

$^1$H-NMR (DMSO-d$_6$): 11.61 (s, 1H, H3), 10.07 (distorted t, 1H, NHTFA), 8.35 (s, 1H, H6), 7.26 (s, 0.39H, CHCl$_3$), 5.89 (dd, J=6.6 and 3.2, 1H, H1'), 5.15 (t, J=5.2, 1H, 5'OH), 4.22 (broad d, 2H, —CH$_2$N—), 4.04 (apparent hept, J=3.5, 1H, H4'), 3.73, and 3.53 (m, 1H, H5'), 2.26, 2.03 and 1.84 (m, 4H, H2' and H3'). TLC (95:5 dichloromethane-methanol, two elutions, UV): Starting iodide 21, R$_f$=0.37; product 22, 0.28; catalysts, 0.95 and 0.80 plus slight streakiness.

C. PREPARATION OF 5-(3-AMINO-1-PROPYNYL)-2',3'-DIDEOXYURIDINE 5'-TRIPHOSPHATE (5-AP3-ddUTP, 23)

Alkynylamino nucleoside 22 (0.30 mmol) was converted to the corresponding triphosphate and its trifluoroacetyl group was removed following the general procedure given in Example 5E. After addition of the second aliquot of phosphorus oxychloride, phosphorylation was allowed to proceed for 210 minutes. Assuming an absorption coefficient for the product equal to that of the starting material (13,000), the yield of triphosphate 23, based on its UV absorption at 291.5 nm, was 18%.

EXAMPLE 7
PREPARATION OF 7-(3-AMINO-1-PROPYNYL)-2',3'-DIDEOXYGUANOSINE 5'-TRIPHOSPHATE (7-AP3-ddc7GTP)

A. PREPARATION OF 6-METHOXY-2-METHYLTHIO-9-(3,5-DI-O-p-TOLUOYL-2-DEOXY-β-D-RIBOFURANOSYL)-7-DEAZAPURINE (24)

6-Methoxy-2-methylthio-7-deazapurine (9.2 g, prepared following the procedure of F. Seela and R. Richter, Chem. Ber., 111, 2925 (1978)) was azeotropically dried by dissolving in 150 mL of dry pyridine and evaporating to dryness at 30°–35°. This material was suspended in 450 mL of dry acetonitrile at room temperature under nitrogen and sodium hydride (2.16 g of a 60% suspension in oil) was added with stirring. After 45 minutes, 1-chloro-2-deoxy-3,5-di-O-p-toluoyl-α-D-ribofuranose (18.6 g, prepared following the procedure of M. Hoffer, Chem. Ber., 93, 2777 (1960)) was added in three equal portions over a 20 minutes. After stirring the reaction mixture for an additional 45 minutes at room temperature, acetic acid (1 mL) and dichloromethane (300 mL) were added. The mixture was suction filtered through a pad of filter-aid, and the filtrate was evaporated to dryness. The residue was dissolved in benzene and this solution was washed with water (2×) and brine (1×). After drying the organic layer over sodium sulfate and evaporating, the residue was dissolved in methanol (400 mL) and allowed to crystallize affording 19.24 g (73.8%) of ribosylated product 24 as colorless crystals (mp 106°–107°).

$^1$H-NMR (CDCl$_3$, 360 MHz): 2.42 (s, 3H, toluoyl CH$_3$), 2.44 (s, 3H, toluoyl CH$_3$), 2.64 (s, 3H, SCH$_3$), 2.70 and 2.89 (m, 2H, H2'), 4.08 (s, 3H, OCH$_3$), 4.56, (m, 1H, H3'), 4.65 (m, 2H, H5'), 5.74 (m, 1H, H4'), 6.44 (d, J=4, 1H, H7), 6.77 (dd, J=8 and 6, 1H, H1'), 7.05 (d, J=4, 1H, H8) and 7.25 and 7.95 (m, 8H, toluoyl H). Recrystallization of a sample of the above material from methanol containing a small amount of dichloromethane afforded crystals of mp 109°–110°.

B. PREPARATION OF 6-METHOXY-2-METHYLTHIO-9-(2-DEOXY-β-D-RIBOFURANOSYL)-7-DEAZAPURINE (25)

A suspension of ester 24 (19 g) and the hydroxide form of a strongly basic anion exchange resin (38 g of Rexyn 201) in 600 mL of methanol was refluxed for 1.5 hour under nitrogen. The hot suspension was suction filtered to remove the resin and the filtrate was evaporated to dryness. The solid residue was dissolved in ether (450 mL) and, after 10 minutes, the solution was filtered through a pad of filter aid to remove a small amount of a colored impurity. The solution was seeded with crystals of the desired product obtained from a previous reaction and allowed to stand overnight at 25°. Crystalline diol 25 was collected by filtration and the mother liquor was concentrated to afford a second crop. Each crop was washed thoroughly with ether and dried to afford a total of 8.43 g (78.0%) of diol 25 as colorless crystals (mp 129°–130°).

$^1$H-NMR (DMSO-d$_6$, 360 MHz): 2.21 and 2.55 (m, 2H, H2'), 2, 56 (s, 3H, SCH$_3$), 3.53 (m, 2H, H5'), 3.82 (m, 1H, H3'), 4.02 (s, 3H, OCH$_3$), 4.36 (m, 1H, H4'), 4.90 (t, J=5.5, 1H, 5'OH), 5.30 (d, J=5.5, 1H, 3'OH), 6.48 (d, J=4, 1H, H7), 6.55 (dd, J=8 and 6, 1H, H1'), 7.48 (d, J=4, 1H, H8). Recrystallization of a sample of this material from dichloromethane containing a small amount of methanol afforded crystals of mp 130°–131°=.

C. PREPARATION OF 6-METHOXY-2-METHYLTHIO-9-(5-O-TRIPHENYLMETHYL-2-DEOXY-β-D-RIBOFURANOSYL)-7-DEAZAPURINE (26)

Diol 25 (7.2 g) was azeotropically dried by dissolving in dry pyridine and evaporating the solution to dryness at 35°. The residue was dissolved in dry pyridine (100 mL) and triphenylmethyl chloride (8.0 g), triethylamine (4.0 mL), and 4-(dimethylamino)pyridine (300 mg) were added. After heating the reaction mixture at 65° under nitrogen for 30 minutes, a second addition of triphenylmethyl chloride (1.0 g) was made and heating was continued for 16.5 hours. After cooling, the reaction mixture was concentrated and the residue was partitioned between dichloromethane and water. The aqueous layer was extracted with dichloromethane and the combined organic layers were washed with 0.3N hydrochloric acid, aqueous sodium bicarbonate, and brine. After drying over sodium sulfate and concentrating, purification of the crude product by chromatography on silica gel with 0%, 1%, 1.5% and 2% methanol in dichloromethane afforded 12.1 g (94.5%) of monotrityl ether 26 as a colorless glass.

$^1$H-NMR (CDCl$_3$, 300 MHz): 2.58 (s, 3H, SCH$_3$), 2.42 and, 2.62 (m, 2H, H2'), 3.37 (m, 2H, H5'), 4.04 (m, 1H, H3'), 4.08 (s, 3H, OCH$_3$), 4.60 (m, 1H, H4'), 6.40 (d, J=4, 1H, H7), 6.68 (apparent t, J=7, 1H, H1'), 7.00 (d, J=4, 1H, H8), 7.27 and 7.43 (m, 15H, trityl H). This data was obtained from a different batch of 26 prepared as described above.

D. PREPARATION OF 6-METHOXY-2-METHYLTHIO-9-(5-O-TRIPHENYLMETHYL-2,3-DIDEOXY-β-D-RIBOFURANOSYL)-7-DEAZAPURINE (27)

A solution of trityl ether 26 (12.1 g), 4-dimethylaminopyridine (9.2 g), and phenyl chlorothionocarbonate (7.5 mL, Aldrich) dry dichloromethane (220 mL) was stirred at 25° for 2 hours under nitrogen. Since TLC analysis indicated that the reaction was incomplete, phenyl chlorothionocarbonate (4.0 mL) was added and the reaction mixture was stirred for an additional 1 hour. The solution was diluted with dichloromethane (280 mL) and washed sequentially with 0.5N hydrochloric acid (500 mL), 0.5N sodium hydroxide (500 mL), and brine. The organic layer was dried over sodium sulfate and evaporated to dryness.

The resulting crude thionocarbonate was dissolved in dry toluene (350 mL) and azoisobisbutyronitrile (350 mg) and tri-n-butyltin hydride (10 mL) were added. The resulting solution was heated at 100°–105° for 10 minutes. After cooling, the solution was diluted with a little ether and was shaken with 10% aqueous potassium fluoride (350 mL). The two layers were filtered through a pad of filter aid (to remove a dark sludge) and separated. The organic layer was washed with 0.75N potassium hydroxide and brine, dried over sodium sulfate and concentrated. Chromatography of the resulting oil on silica gel with 1:1 dichloromethane-ether and then with dichloromethane afforded 9.93 g (84.5%) of dideoxynucleoside 27 as a colorless solid (mp 122°–124°).

$^1$H-NMR (CDCl$_3$, 360 MHz): 2.10, 2.33, and 2.43 (m, 4H, H2' and H3'), 2.60 (s, 3H, SCH$_3$), 3.30 (m, 2H, H5'), 4.08 (s, 3H, OCH$_3$), 4.29 (m, 1H, H4'), 6.36 (d, J=3.7, 1H, H7), 6.53 (dd, J=7 and 4, 1H, H1'), 7.09 (d, J=3.7, 1H, H8), 7.25 and 7.45 (m, 15H, trityl H).

E. PREPARATION OF 7-IODO-6-METHOXY-2-METHYLTHIO-9-(5-O-TRIPHENYLMETHYL-2,3-DIDEOXY-β-D-RIBOFURANOSYL)-7-DEAZAPURINE (28)

N-Iodosuccinimide (10.0 g) was added to a solution of deazapurine 27 (9.9 g) in dry dimethylformamide (550 mL). After stirring in the dark under nitrogen for 16 hours, 10% aqueous sodium bicarbonate (2.5 mL) was added and the reaction mixture was concentrated in vacuo at 50° to a volume of 100 mL. This solution was partitioned between water and ethyl acetate. The organic layer was washed with 5% aqueous sodium hydrosulfite and brine, dried over sodium sulfate, and concentrated. Chromatography of the slightly impure product on silica gel with dichloromethane afforded 11.68 g (95.6%) of iodide 28 as a colorless glassy solid.

$^1$H-NMR (CDCl$_3$, 300 MHz): 2.06, 2.24, and 2.41 (m, 4H, H2' and H3'), 2.58 (s, 3H, SCH$_3$), 3.30 (m, 2H, H5'), 4.10 (s, 3H, OCH$_3$), 4.29 (m, 1H, H4'), 6.47 (dd, J=6 and 4, 1H, H1'), 7.19 (s, 1H, H8), 7.30 and 7.46 (m, 15H, trityl H). This data was obtained from a different batch of 28 prepared as described above.

F. PREPARATION OF 7-IODO-2-METHYLTHIO-9-(5-O-TRIPHENYL-METHYL-2,3-DIDEOXY-β-D-RIBOFURANOSYL)-7-DEAZAPURI-4-ONE (29)

Sodium thiocresolate was prepared by adding sodium methoxide (1 eq) to a solution of thiocresol in methanol and then evaporating to dryness. A mixture of methyl ether 28 (4.0 g), sodium thiocresolate (4.0 g), and hexamethylphosphoramide (10 mL) in dry toluene (150 mL) was refluxed under nitrogen for 4.5 hours. After cooling, the mixture was partitioned between ethyl acetate and water. The organic layer was washed with water and brine, dried over sodium sulfate, and evaporated to dryness. Chromatography of the resulting crude product on silica gel with 0% and 2% methanol in dichloromethane afforded 3.80 g (97.0%) of deazapurinone 29 as a colorless glassy solid.

$^1$H-NMR (CDCl$_3$, 360 MHz): 2.05, 2.25, and 2.42 (m, 4H, H2' and H3'), 2.60 (s, 3H, SCH$_3$), 3.30 (m, 2H, H5'), 4.28 (m, 1H, H4'), 6.40 (dd, J=7 and 4, 1H, H1'), 7.05 (s, 1H, H8), 7.30 and 7.46 (m, 15H, trityl H), 10.00 (broad s, 1H, H1).

G. PREPARATION OF 7-IODO-5'-O-TRIPHENYLMETHYL-2',3'-DIDEOXY-7-DEAZAGUANOSINE (30)

Meta-chloroperoxybenzoic acid (1.23 g, 85%, Aldrich) was added to a stirred solution of methylthio ether 29 (3.6 g) in dry dichloromethane (150 mL) at 0° under nitrogen. After 15 minutes, the cooling bath was removed and stirring was continued at 25° for 40 minutes. This solution was washed with aqueous sodium bicarbonate and brine and dried over sodium sulfate. Methanol (two percent by volume) was added and the resulting solution was passed through a short plug of silica gel to remove polar impurities. The resulting crude sulfoxide (3.07 g) was dissolved in dioxane (40 mL) and placed in a glass-lined bomb. Ammonia (10.0 g) was added and the mixture was heated at 100° for 2 hours in an autoclave. The resulting solution was evaporated to dryness. The residue was dissolved in dichloromethane (20 mL) and filtered through a pad of filter-aid. Methanol (40 mL) was added to the solution and, on cooling, 1.57 g of colorless product crystallized. The mother liquor was evaporated and purified by medium pressure liquid chromatography on silica gel with 5% methanol in dichloromethane to afford an additional 328 mg of product as colorless crystals. The total yield of deazaguanosine 30 was 1.90 g (55.4%).

$^1$H-NMR, (CDCl$_3$, 300 MHz): 2.05, 2.23, and 2.35 (m, 4H, H2' and H3'), 3.29 (m, 2H, H5'), 4.26 (m, 1H, H4'), 5.90, (broad s, 1H, NH$_2$), 6.24 (dd, J=7 and 4, 1H, H1'), 6.90 (s, 1H, H8), 7.30 and 7.46 (m, 15H, trityl H) 10.90 (broad s, 1H, H1). Recrystallization of a sample of this material from methanol-dichloromethane afforded crystals of mp 201°-203°.

H. PREPARATION OF 2',3'-DIDEOXY-7-IODO-7-DEAZAGUANOSINE (31)

A solution of trityl ether 30 (1.7 g) in formic acid (12 mL) was stirred at room temperature for 10 minutes. The resulting yellow suspension was then quickly evaporated to dryness in vacuo at 30°. Chromatography of the residue on silica gel with 5%, 7%, and 10% methanol in dichloromethane afforded 940 mg of a colorless solid. Trituration of this solid with ether containing a little dichloromethane yielded 838 mg (81.0%) of nucleoside 31 as colorless crystals.

$^1$H-NMR (DMSO-d$_6$, 360 MHz): 1.95, 2.09, and 2.26 (m, 4H, H2', and H3'), 3.48 and 3.54 (m, 2H, H5'), 3.98 (m, 1H, H4'), 4.90 (broad t, J=5, 1H, 5'OH), 6.08 (m, 1H, H1'), 6.32 (broad s, 2H, NH$_2$), 7.12 (s, 1H, H8), 10.46 (broad s, 1H, H1).

I. PREPARATION OF 7-(3-TRIFLUOROACETAMIDO-1-PROPYNYL)-2',3'-DIDEOXY-7-DEAZAGUANOSINE (32)

Iodide 31 (376 mg, 1.00 mmol) was coupled for 2.25 hours to N-propargyltrifluoroacetamide by the general method given in Example 5C. Product and starting material were indistinguishable by TLC, so the reaction was monitored by reverse phase HPLC (10 cm ODS, 1 mL/minute, gradient from 100% water to 100% methanol over 5 minutes, then 100% methanol, with UV detection at 280 nm: starting iodide 31, 5.49 minutes; product 32, 5.75 minutes; intermediate, 6.58 minutes). The crude product was poorly soluble in dichloromethane, so it was concentrated from a dichloromethane-methanol solution onto 5 g of silica gel before being loaded onto the chromatography column. Elution with 2%, 5%, 7% and 10% methanol in dichloromethane afforded 300 mg (78%) of alkynylamino nucleoside 32 as a yellow solid.

$^1$H-NMR (DMSO-d$_6$, 360 MHz): 1.96, 2.08, and 2.28 (m, 4H, H2' and H3'), 3.47 and 3.55 (m, 2H, H5'), 3.99 (m, 1H, H4'), 4.22 (broad s, 2H, —CH$_2$—), 4.90 (t, J=5, 1H, 5'OH), 6.09 (dd, J=6 and 4, 1H, H1'), 6.33 (broad s, 2H, NH$_2$), 7.30 (s, 1H, H8), 10.05 (broad s, 1H, NHTFA), 10.50 (broad s, 1H, H1).

$^1$H-Decoupled $^{13}$C-NMR (DMSO-d$_6$): 155.5 (q, J=36.5, trifluoroacetyl carbonyl), 157.8, 153.1 and 149.9 (C2, C4 and C6), 122.6 (C8), 115.9 (q, J=288, CF3), 99.4 and 97.5 (C7 and C5), 84.2 and 77.4 (acetylenic), 83.2 and 81.0 (C1' and C4'), 62.9 (C5'), 29.7 (propargylic), 31.8 and 25.8 (C2' and C3'). This $^{13}$C-NMR data was obtained from a different batch of 32 prepared as described above.

J. PREPARATION OF 7-(3-AMINO-1-PROPYNYL)-2',3'-DIDEOXY-7-DEAZAGUANOSINE 5'-TRIPHOSPHATE (7-AP3-ddc7GTP)

Alkynylamino nucleoside 32 (0.90 mmol) was converted to the corresponding 5'-triphosphate and the trifluoroacetyl protecting group was subsequently removed following the general procedure given in Example 5F. After the second addition of phosphorus oxychloride, the reaction was stirred for an additional 165 minutes. Assuming an absorption coefficient for the product equal to that of the starting material (11,900), the yield of 7-AP3-ddc7GTP, based on its absorption at 272.5 nm, was 18%.

EXAMPLE 8

PREPARATION OF 7-(3-AMINO-1-PROPYNYL)-2',3'-DIDEOXY-7-DEAZAADENOSINE 5'-TRIPHOSPHATE (7-AP3-ddc7ATP)

A. PREPARATION OF 2'-ACETOXY-3'-BROMO-5'-(2-ACETOXYISOBUTYRYL)ADENOSINE (33)

2-Acetoxyisobutyryl bromide (19.5 mL, 150 mmol, 5 eq, prepared according to the procedure of Russell et al, J. Am. Chem Soc., 95, 4016-4030 (1973)) was added over 15 minutes to a suspension of tubercidin (7-deazaadenosine, 6.66 g, 25.0 mmol, Sigma) in dry acetonitrile (250 mL, Aldrich). The suspended solid dissolved in about 5 minutes and the reaction was stirred under nitrogen for 22 hours at 25°. The reaction mixture was added to a solution of dipotassium hydrogen phosphate (43.55 g, 300 mmol, 6 eq) in water (400 mL). After stirring for 30 minutes, the reaction mixture was extracted with ethyl acetate (1×400 mL and 2×200 mL). The combined organic layers were dried over magnesium sulfate and evaporated to dryness to afford 14.73 g (118%) of white foam. This material was greater than 95% one slightly broadened spot by TLC (with UV detection), but NMR showed that one major and at least one minor product were present. The NMR spectrum was consistent with the major product being bromoacetate 33.

$^1$H-NMR (DMSO-d$_6$) for the major component 33: 8.08 (s, 1H, H2), 7.34 (d, J=3.7, 1H, H8), 7.12 (broad s, 2H, NH$_2$), 6.70 (d, J=3.7, 1H, H7), 6.32 (d, J=3.8, 1H, H1'), 5.61 (dd, J=2.4 and 3.8, 1H, H2'), 4.89 (dd, J=2.4 and 4.5, 1H, H3'), 4.43 (m, 1H, H4'), 4.35 (dd, J=12 and 4, 1H, H5'a), 4.29 (dd, J=12 and 7, 1H, H5'b), 2.08 (s, 3H, OAc), 2.00 (s, 3H, OAc), and 1.49 (s, 6H, 2CH$_3$).

B. PREPARATION OF 2',3'-DIDEOXY-2',3'-DIDEHYDRO-7-DEAZAADENOSINE (34)

Zinc-copper couple was freshly prepared by rapidly (total elapsed time of about 10 minutes) washing zinc dust (20 g, Mallinkrodt) with 1N hydrochloric acid (3×50 mL), water (2×50 mL), 2% cupric sulfate (2×50 mL), water (4×50 mL), ethanol (3×50 mL) and ether (2×50 mL). During each wash, the zinc dust was stirred in a fritted funnel until it was suspended and the wash was removed by suction while minimizing exposure of the zinc to air. The couple was vacuum-dried for 30 minutes. The above crude bromoacetate (14.63 g) was dissolved in dry dimethylformamide (150 mL, Aldrich) and approximately 25 mL of solvent was removed with a rotary evaporator (45°, at 2 torr). Fresh zinc-copper couple (14.63 g, about 9 eq) was added and the resulting suspension was stirred under nitrogen at 25°. Depending on the quality of the zinc-copper couple, this reaction can show an induction period and/or variable rate, so the reaction was allowed to proceed until TLC (90:9:1 dichloromethane-methanol-concentrated ammonium hydroxide: starting material R$_f$=0.45 and products R$_f$=0.39 and 0.36) indicated the starting material had been completely consumed. In this case, the reaction was complete in less than 15 minutes. After 100 minutes, saturated aqueous sodium bicarbonate (75 mL) was added carefully over 10 minutes to the reaction mixture. The reaction mixture was filtered through a filter aid and the filter aid was washed with methanol (2×50 mL). The combined filtrates were evaporated to dryness and the residue was partitioned between water (150 mL) and ethyl acetate (150 mL). The aqueous layer was extracted with ethyl acetate (2×100 mL) and the combined organic extracts were dried over magnesium sulfate, concentrated, and vacuum dried for 1 hour.

The resulting dark orange semisolid was dissolved in methanol (100 mL) and then water (25 mL) and Rexyn 201 resin (29 g, 4.3 meq/g, 5 eq, hydroxide form) were added. The reaction mixture was refluxed for a total of 210 minutes. Monitoring by TLC (85:13:2 dichlormethane-methanol-concentrated ammonium hydroxide: intermediate ester, R$_f$=0.49; final product 34, 0.24) indicated that the reaction had rapidly halted at about 70% conversion, so after 165 minutes, an additional 29 g of resin was added. Without cooling, the resin was removed by filtration and washed with 1:1 dichloromethane-methanol (2×75 mL). The combined filtrates were evaporated to dryness and the resulting purple solid was recrystallized from boiling isopropanol (150 mL) to afford 3.778 g of olefin 34 as a off-white needles (mp 205°-206°). A second crop of 0.631 g (pale purple needles, mp 202°-203°) was obtained by concentrating the mother liquors to 25 mL. Both crops (total 4.409 g, 76%) were homogeneous by TLC and pure by NMR except for a trace of isopropanol.

$^1$H-NMR (DMSO-d$_6$): 8.07 (s, 1H, H2), 7.15 (d, J=3.6, 1H, H8), 7.12 (broad s, 1H, H1'), 7.01 (broad s, 2H, NH$_2$), 6.57 (d, J=3.6, 1H, H7), 6.43 and 6.02 (broad d, J=6.0, 1H each, H2' and H3'), 4.95 (t, J=6.5, 1H, 5'OH), 4.79 (m, 1H, H4'), and 3.52 (m, 2H, H5').

C. PREPARATION OF 2',3'-DIDEOXY-7-DEAZAADENOSINE (35)

A 450-mL Parr bottle was charged with olefin 34 (3.80 g), ethanol (76 mL), 10% palladium on carbon (380 mg, Aldrich) and 40 psi of hydrogen. After shaking for 4.67 hours at 25°, 14.5 psi of hydrogen had been absorbed and hydrogen uptake had ceased. TLC (two elutions with 85:13:2 dichloromethane-methanol-concentrated ammonium hydroxide: starting material 34, 0.45; product 35, 0.48) showed complete conversion to a single UV-active new product. The catalyst was removed by filtration through filter aid and washed with ethanol. Removal of solvent from the filtrate and vacuum drying overnight afforded 3.98 g (104%) of dideoxynucleoside 35 as a white foam. NMR indicated that the product was homogeneous except for the presence of 8 wt % of ethanol (96% corrected yield). Similar batches of this material resisted crystallization and became extremely hygroscopic upon azeotropic drying with anhydrous solvents. Therefore this material was stored under vacuum for about 1 week and used when NMR indicated that the material contained 5 wt % of ethanol. The lack of crystallinity and spectral characteristics observed for this product were in accord with those reported previously by Robins et al., Can. J. Chem., 55, 1259 (1977).

$^1$H-NMR (DMSO-d$_6$): 8.04 (s, 1H, H2), 7.33 (d, J=3.6, 1H, H8), 6.97 (broad s, 2H, NH$_2$), 6.56 (d, J=3.6, 1H, H7), 6.34 (dd, J=5.2 and 6.4, 1H, H1'), 4.96 (t, J=5.6, 1H, 5'OH) 4.33 (t, J=5.1, 0.43H, ethanol OH), 4.04 (m, 1H, H4'), 3.4-3.6 (m, 2.86H, H5' and ethanol CH$_2$), 2.33, 2.21 and 2.02 (m, 4H, H2' and H3'), and 1.06 (t, J=7.0, 1.3H, ethanol CH$_3$).

D. PREPARATION OF 7-IODO-2',3'-DIDEOXY-7-DEAZAADENOSINE (36)

A mechanically-stirred solution of 95% pure dideoxynucleoside 35 (2.95 g, 11.96 mmol), anhydrous sodium acetate (4.13 g, 50.3 mmol, 4 eq), and mercuric acetate (3.81 g, 11.95 mmol, 1.00 eq, Fisher, 99.9%) in water (190 mL) was heated under nitrogen at 65° for 2 hours. After cooling the resulting white suspension of mercurial to 25°, iodine (4.79 g, 18.9 mmol, 1.6 eq) and ethyl acetate (190 mL) were added. After 1 hour, the suspended mercurial had been consumed and a clear purple solution remained. After 2 hours, sodium sulfite (6.35 g) was added and the purple color disappeared. After stirring for 30 minutes, hydrogen sulfide gas was gently bubbled into the reaction for 15 minutes. Mercuric sulfide (a black colloid) and iodide 36 (a white powder) precipitated from the reaction. Complete precipitation of mercury(II) was assessed by TLC by monitoring the disappearance of one of the two major UV-active spots. The reaction mixture was filtered through filter aid and separated into two layers. The filter aid was washed with boiling ethyl acetate (9×100 mL) until TLC indicated that no further product was being extracted. Each ethyl acetate extract was washed with the aqueous layer. The combined ethyl acetate layers were dried over magnesium sulfate and evaporated to dryness. The resulting crude solid turned red upon exposure to air. This material was dissolved in 3:1 dichloromethane-methanol (100 mL) and the free base form of a weakly basic anion exchange resin (5.0 g, BioRad AG3 X4A, 2.9 meq/g dry) was added. Hydrogen sulfide was bubbled into the red solution for 10 minutes and the red color was discharged. A slight cloudiness was eliminated by briefly warming and the solution was rapidly filtered through a 2 cm plug (15 g) of silica gel. The silica gel was eluted with additional 3:1 dichloromethane-methanol (100 mL). Silica gel (50 g) was added to the filtrate and hydrogen sulfide was bubbled in for 10 minutes. The solvent was removed from this mixture with a rotary evaporator and the silica gel was "dried" by co-evaporating with chloroform (200 mL). This silica gel was rapidly loaded onto a silica gel column (500 g) which had been degassed with a stream of nitrogen. Elution under nitrogen with 5% (6 L) and 10% (4 L) methanol in dichloromethane afforded 2.92 g (64%) of iodide 36 as a white powder and 456 mg (7.5%) of less polar 7,8-diiodo-2',3'-dideoxy-7-deazaadenosine. Recrystallization of the major product from boiling ethyl acetate (200 mL) afforded 2.626 g of white needles (mp 158°–160°). Concentration of the mother liquors to 10 mL afforded a second crop of 0.391 g of light red needles (mp 156°–158°). Both crops were homogeneous according to NMR and TLC and together represent a 64% overall yield from olefin 34.

$^1$H-NMR (DMSO-d$_6$): 8.09 (s, 1H, H2), 7.67 (s, 1H, H8), 6.65, (broad s, 2H, NH$_2$), 6.34 (dd, J=4.4 and 6.8, 1H, H1'), 4.95 (t, J=5.5, 1H, 5'OH), 4.04 (apparent hept, J=3.5, 1H, H4'), 3.59 and 3.49 (m, 1H, H5'), 2.30, 2.28 and 2.00 (m, 4H, H2' and H3').

E. PREPARATION OF 7-(3-TRIFLUOROACETAMIDO-1-PROPYNYL)-2',3'-DIDEOXY-7-DEAZAADENOSINE (37)

Iodide 36 (720.3 mg, 2.00 mmol) was coupled for 90 minutes with N-propargyltrifluoroacetamide following the standard procedure given in Example 5C. Chromatography with 7% methanol in dichloromethane afforded 705.8 mg (92%) of coupling product 37 as an off white powder which was homogeneous according to NMR and TLC. Recrystallization from boiling ethyl acetate (10 mL) afforded 372 mg of white microcrystals (mp 169°–171°).

$^1$H-NMR (DMSO-d$_6$): 10.1 (distorted t, 1H, NHTFA), 8.10 (s, 1H, H2), 7.78 (s, 1H, H8), 6.0–7.5 (very broad s, NH$_2$), 6.34 (dd, J=4.5 and 7.0, 1H, H1'), 4.98 (t, J=5, 1H, 5'OH), 4.31 (slightly broadened s, 2H, —CH$_2$N—), 4.10 (apparent hept, J=3.5, 1H, H4'), 3.60, and 3.40 (m, 1H, H5'), 2.37, 2.18 and 2.00 (m, 4H, H2' and H3'). TLC (90:9:1 dichloromethane-methanol-concentrated ammonium hydroxide;UV): starting iodide 36, R$_f$=0.36; product 37, 0.26).

F. PREPARATION OF 7-(3-AMINO-1-PROPYNYL)-2',3'-DIDEOXY-7-DEAZAADENOSINE 5'-TRIPHOSPHATE (7-AP3-ddc7ATP)

Alkynylamino nucleoside 37 (1.00 mmol) was converted to the corresponding 5'-triphosphate and the trifluoroacetyl group was removed following the general procedure described in Example 5E. After addition of the second aliquot of phosphorus oxychloride, the solution was stirred for 120 minutes. Assuming an absorption coefficient for the product equal to that of the starting material (12,700), the yield of 7-AP3-ddc7ATP, based on the absorption at 279.5 nm, was 40%.

$^1$H-NMR (D$_2$O): 7.97 (s, 1H, H2), 7.80 (s, 1H, H8), 6.33 (m, 1H, H1'), 4.44 (m, 1H, H4'), 4.27 (m, 1H, H5'a), 4.14 (m, 1H, H5'b), 4.11 (broad s, 2H, —CH$_2$—), 2.6–2.0 (m, 4H, H2' and H3'), plus counterion (triethylammonium) peaks. $^{31}$P-NMR (D$_2$O): −8.59 (broad d, J=20, 1P), −9.56 (d, J=20, 1P), and −21.38 (m, 1P). UV (pH 8.2 aq Tris): maxima at 238 and 279.5 nm.

EXAMPLE 9

General Coupling Procedure for Preparation of a Fluorescent-labeled Chain Terminator Preparation of a T-Terminator: 5-(SF-505-Sar-AP3) ddUTP The amine 5-(AP3)ddUTP (60 micromole) from Example 6C was taken up in water (0.300 mL) and diluted with DMF (0.600 mL). A solution of dye-labeling reagent Ac2EtSF-505-Sar-NHS (72 mg, 126 micromole) from Example 1E in DMF (0.600 mL) was added and the mixture was stirred at 50° C. for 4 hours. Concentrated aqueous ammonia (1.5 mL) was added, the flask was tightly stoppered, and heating was continued at 50° C. for 20 minutes. The resulting red solution was diluted to 60 mL with water and applied to column of DEAE-Sephadex A-25-120 (1×35 cm bed) that had been equilibrated with 2.0M pH 7.7 aqueous TEAB (50 mL) and then 0.2M pH 7.7 aqueous TEAB (50 mL). The column was eluted with a linear gradient of pH 7.7 aqueous TEAB: 0.2M (150 mL)→2.0M (150 mL). The column was driven at 100 mL/hour collecting fractions every 3 minutes. The eluent was monitored by absorbance at 510 nm (40 AUFS). Two lesser by-product bands eluted first followed by the stronger product band with nearly baseline resolution. The fractions estimated to contain pure product were pooled, stripped down (T<30° C.), coevaporated with absolute ethanol (3×), and taken up in a small volume (5.2 mL) of water. The solution was assayed by visible absorption (pH 8.2 50 mM aq Tris buffer) and lyophilized. A dilute solution of the product displayed an absorption maximum at 491 nm. The yield, calculated assuming the free dye absorption coefficient (72,600), was 31 micromoles (51%).

Additional fluorescent-labeled chain terminator compounds were prepared according to the general procedure disclosed. The nomenclature in Table 1 represents the fluorescent-labeled spacer (e.g. SF-512-Sar) and dideoxynucleotide-linker (AP3-ddNTP) materials which were prepared in the preceding examples and combined according to the general procedure to prepare new compositions useful in sequencing DNA.

EXAMPLE 10

CHARACTERIZATION OF PHIX174 RF I DNA USING FOKI AS THE PRIMARY CLEAVAGE ENZYME AND ALUI AS THE SECONDARY CLEAVAGE ENZYME.

A quantity of 15 μg phiX174 RF I DNA (New England BioLabs; 1 μg/μL) was dispensed into a 1.5 mL Eppendorf tube. Added to this was 20 μL 10X FokI reaction buffer (200 mM KCl; 100 mM Tris-HCl, pH 7.5; 100 mM MgCl2; 60 mM beta-mercaptoethanol; 1 mg/mL bovine serum albumin), 145 μL sterile distilled H2O, and 20 μL of restriction enzyme FokI (New England Biolabs; 6 units/μL). This reaction was incubated at 37 degrees Centigrade for 4 hours. After a 10 minute incubation at 68 degrees Centigrade to inactivate the restriction enzyme, the reaction was cooled to room temperature and an equal volume of 5M ammonium acetate was added. Added to this mixture was 2.5 volumes of cold 100% ethanol. After vortexing, the tube was placed in dry ice for 15 minutes, then centrifuged (14,000 rpm) for 15 minutes. After discarding the ethanol supernatant, 0.5 ml of 70% ethanol was added and the tube vortexed for 5 seconds. The tube was spun 15 minutes in a microcentrifuge, the DNA pellet vacuum dried and resuspended in 15 μL TE buffer (10 mM Tris-HCl, pH 8.0; 1 mM EDTA). This gives a stock preparation of FokI digested phiX174 DNA.

0.5 μg of the phiX174 FokI digest was dispensed into a 1.5 mL Eppendorf tube. Added to this was 4.5 μL sterile distilled H2O, 2 μL of a 5X reaction buffer (0.3 M Tris-HCl, pH 8.3; 0.375M NaCl; 0.0375M MgCl2; 0.025M dithiothreitol), 1 μL of a solution containing 10 μM dATP, 25 μM dCTP, 50 μM dGTP and 10 μM dTTP in 50 mM Tris-HCl, pH 7.8, 1 μL of a solution containing the four fluorescent-labeled chain terminators [7-(SF505-Sar-AP3)ddc7GTP, 7-(SF512-Sar-AP3)ddc7ATP, 5-(SF519-Sar-AP3)ddCTP, and 5-(SF526-Sar-AP3)ddTTP526 described previously] at a concentration of 250 μM each, and 1 μL avian myeloblastosis virus reverse transcriptase (New England Nuclear; 17 units/μL). The reaction was incubated at 42 degrees Centigrade for 30 minutes. The DNA was precipitated by adding 10 μL 5M ammonium acetate plus 50 μL ethanol, mixing, and placing on dry ice for 10 minutes. the DNA was recovered by centrifuging at 14,000 rpm for 15 minutes. After discarding the supernatant, the DNA pellet was rinsed with 500 μL 70% (v/v) ethanol, dried under vacuum for 10 minutes, then dissolved in 16 μL TE. Secondary cleavage with AluI was accomplished by adding 2 μL 10X AluI reaction buffer (0.5M NaCl; 0.06M Tris-HCl, pH 7.6; 0.06M MgCl2; 0.06M 2-mercaptoethanol; 1 mg/ml bovine serum albumin), and 2 μL restriction enzyme AluI (New England BioLabs; 10 units/μL). The reaction was incubated at 37° C. for 1 hour.

After the addition of 30 μL of sterile distilled water, the reaction was passed through a G-25 Select-D spin column (5 Prime-3 Prime; Paoli, PA) which had been prewashed with sterile distilled water, to separate unincorporated fluorescent-labeled chain terminators from fluorescent-labeled DNA fragments in the reaction mixture. The column was washed with 50 μL of sterile distilled water. The combined column effluents were collected and vacuum dried. A 0.5 mL quantity of 70% ethanol was added and the tube vortexed for 5 seconds. The tube was then spun for 10 minutes in a microcentrifuge, the DNA pellet vacuum dried and resuspended in 10 μL 95% formamide-25 mM EDTA. The tube was heated at 68 degrees Centigrade for 10 minutes and 3 μL of the DNA sample micropipetted onto a preconditioned 6% polyacrylamide:bis (19:1) gel (15 cm×40 cm×0.35 mm) containing 8.0M urea and 1X TBE buffer. The sample was electrophoresed at 27 watts. The techniques of Prober et al. as exemplified by the Genesis 2000 TM of using gel electrophoresis, the irradiation of the gel by an argon ion laser, and the detection of fluorescent emissions were used to identify the reporters on each DNA fragment. The sizes of the labeled fragments were determined by comparison to the mobilities of known size standards run in a parallel lane of the gel. Table I shows a representative list of detected fragments indicating the size of each fragment, the ratio of the signals from the two detectors, and the 3' terminal base deduced from the ratio. The output appears as quarters of peaks because FokI generates a four-base 5' overhang. The distribution of fragments and the identities of the 3' terminal bases are exactly as predicted from the known sequence of phiX174 DNA.

TABLE I

| Fragment size, in nucleotides | Ratio of detector signals T channel:R channel | Deduced 3' terminal base |
|---|---|---|
| 21 | 0.16 | C |
| 22 | 0.54 | G |
| 23 | 0.61 | G |
| 24 | 0.09 | T |
| 71 | 0.65 | G |
| 72 | 0.67 | G |
| 73 | 0.15 | C |
| 74 | 0.09 | T |
| 82 | 0.63 | G |
| 83 | 0.28 | A |
| 84 | 0.06 | T |
| 85 | 0.10 | T |
| 116 | 0.16 | C |
| 117 | 0.29 | A |
| 118 | 0.06 | T |
| 119 | 0.07 | T |
| 142 | 0.32 | A |
| 143 | 0.32 | A |
| 144 | 0.07 | T |
| 145 | 0.58 | G |
| 188 | 0.08 | T |
| 189 | 0.56 | G |
| 190 | 0.17 | C |
| 191 | 0.08 | T |
| 205 | 0.34 | A |
| 206 | 0.63 | G |
| 207 | 0.17 | C |
| 208 | 0.17 | C |
| 276 | 0.33 | A |
| 277 | 0.33 | A |
| 278 | 0.07 | T |
| 279 | 0.17 | C |

Thus each fragment is identified not only by size but also by the identity of the labeled 3' nucleotides.

EXAMPLE 11

CHARACTERIZATION OF PHAGE λ DNA USING BSTEII AND BAMHI AS THE PRIMARY CLEAVAGE ENZYMES AND FOKI AS THE SECONDARY CLEAVAGE ENZYME.

Phage λ DNA double digested with the restriction enzymes BstEII and BamHI was prepared in the following manner. A quantity of 20 μg phage λ DNA digested with the restriction enzyme BstEII (New England BioLabs; 0.4 μg/mL) was dispensed into a 1.5 mL Eppendorf tube. Following the addition of 20 μL 10X BamHI reaction buffer (1.5M NaCl; 60 mM Tris-HCl, pH 8.0; 60 mM MgCl$_2$; 1 mg/ml bovine serum albumin), 120 μL H$_2$O, and 10 μL restriction enzyme BamHI (New England BiLabs; 16 units/μL), the reaction was incubated at 37° C. for 2 hours. The DNA was precipitated by adding 200 μL 5M ammonium acetate plus 1 mL ethanol, mixing, and placing on dry ice for 20 minutes. The DNA was recovered by centrifuging at 14,000 rpm for 15 minutes. After discarding the supernatant, the DNA pellet was dried under vacuum for 10 minutes, then dissolved in 79 μL TE (10 mM Tris-HCl, pH 7.4; 1 mM EDTA). The combination of BstEII and BamHI cleaves each phage λ DNA molecule into 19 fragments.

The next step is to incorporate biotin at the ends of the fragments produced by cleavage of phage λ DNA with BstEII and BamHI. This was accomplished by taking the 79 μL sample containing 20 μg phage λ DNA digested with BstEII and BamHI and making the following additions: 10 μL 10X Klenow buffer (0.5M NaCl; 0.1M Tris-HCl, pH 7.5; 0.1M MgCl$_2$; 0.01M dithiothreitol), 5 μL 0.4 mM biotin-11-dUTP (Bethesda Research Laboratories), 5 μL of a solution containing 1 mM dATP, 1 mM dCTP, and 1 mM dGTP, and 1 μL of a solution containing the large fragment (Klenow fragment) of DNA polymerase I (Bethesda Research Laboratories; 6 units/μL). This reaction was incubated at 20° C. for 30 minutes. The DNA was precipitated by adding 100 μL 5 M ammonium acetate plus 500 μL ethanol, mixing, and storing at −20° C. The DNA was recovered by centrifuging at 14,000 rpm for 15 minutes. After discarding the supernatant, the DNA pellet was dried under vacuum for 10 minutes, dissolved in 100 μL TE (10 mM Tris-HCl, pH 7.4; 1 mM EDTA), and passed through a G-50 Select-D spin column (5 Prime-3 Prime, Inc.; Paoli, Pa.). The excluded volume (125 μL) was incubated at 70° C. for 10 minutes, then stored at 4° C. This DNA sample is referred to as phage λ BstEII-BamHI-biotin.

The next step is to perform the secondary cleavage reaction using the restriction enzyme FokI. The following additions were made to the 125 μL phage λ BstEII-BamHI-biotin DNA sample: 20 μL 10X FokI reaction buffer (0.2M KCl; 0.1M Tris-HCl, pH 7.5; 0.1M MgCl$_2$; 0.06M 2-mercaptoethanol; 1 mg/ml bovine serum albumin), 35 μL H$_2$O, and 20 μL restriction enzyme FokI (New England BiLabs; 3 units/μL). The reaction was incubated at 37° C. for 3 hours. The DNA was precipitated by adding 200 μL 5M ammonium acetate plus 1 mL ethanol, mixing, and storing at −20° C. The DNA was recovered by centrifuging at 14,000 rpm for 15 minutes. After discarding the supernatant, the DNA pellet was dried under vacuum for 10 minutes, dissolved in 200 μL TE (10 mM Tris-HCl, pH 7.4; 1 mM EDTA), and stored at 4° C. This provides a stock solution at a DNA concentration of 0.1 μg/μL that will be referred to as phage λ BstEII-BamHI-biotin-FokI. There are 150 FokI cleavage sites in phage λ. Therefore, most of the DNA fragments in the phage λ BstEII-BamHI-biotin-FokI sample do not contain biotin because neither end of most fragments was generated by cleavage with BstEII or BamHI.

The next step is to use incubation with streptavidin-CrO$_2$ particles to separate the relatively few fragments that contain biotin from the bulk of the fragments, followed by the labeling of the free ends with nucleotide-specific fluorescent reporters. Streptavidin was covalently attached to aminosilane coated CrO$_2$ magnetic particles by standard crosslinking with glutaraldehyde as described in Lau et al. U.S. Pat. No. 4,661,408. The DNA sample was diluted by mixing 10 μL (1 μg) of the phage λ BstEII-BamHI-biotin-FokI DNA with 90 μL 100 mM NaCl; 10 mM Tris-HCl, pH 7.4; 1 mM EDTA; 100 μg/ml bovine serum albumin in a siliconized 1.5 mL Eppendorf tube. To this sample was added a suspension of streptavidin-CrO$_2$ particles (10 μg in 10 μL) and the resulting suspension was incubated at room temperature for 15 minutes with shaking followed by 15 minutes at 37° C. The streptavidin-CrO$_2$ particles bearing the biotin-containing DNA fragments were immobilized on the side of the tube by placing the tube in a magnetic rack (MAGIC® Magnetic Separation Unit, Corning Glass Works Magnetic Immunochemistries). After discarding the supernatant, the particles were washed by suspending in 100 μL 100 mM NaCl; 10 mM Tris-HCl, pH 7.4; 1 mM EDTA; 100 μg/ml bovine serum albumin, placing in the magnetic rack, and discarding the supernatant. The washing step was repeated. In order to label the DNA fragments with the fluorescent reporters, the particles were first suspended in 7 μL TE. Then, concentrated stock solutions were added to achieve a 20 μL reaction mixture containing the following final concentrations: 50 mM Tris-HCl, pH 8.3 at 42° C.; 8 mM MgCl$_2$; 30 mM KCl; 1 mM dithiothreitol; 1 μM dATP; 1 μM dCTP, 1 μM dGTP; 1 μM dTTP, 1.67 μM 7-(SF505-Sar-AP3)ddC$^7$GTP; 12.5 μM 7-(SF512-Sar-AP3)ddC$^7$ATP; 2.5 μM 5-(SF519-Sar-AP3)ddCTP; and 10 μM 5-(SF526-Sar-AP3)ddTTP. Following the addition of 1 μL (3 units) reverse transcriptase (New England Nuclear), the reaction was incubated at 42° C. for 1 hour. The sample tube was placed in the magnetic rack to immobilize the particles and the supernatant was discarded. The particles were washed by suspending in 100 μL 0.17% (w/v) Triton X-100; 100 mM NaCl; 10 mM Tris-HCl, pH 7.4; 1 mM EDTA, placing an the magnetic rack, and discarding the supernatant. The washing step with the Triton solution was repeated two times. The labeled fragments were eluted from the particles by suspending the particles in 5 μL 95% (v/v) formamide; 12.5 mM EDTA, incubating at 70° C. for 10 minutes, placing the sample tube in the magnetic rack, and transferring the supernatant containing the labeled fragments to a new tube. The electrophoresis and detection conditions outlined in Example 10 were used to analyze the size and reporter identity for the labeled fragments. Table II shows a representative list of detected fragments indicating the size of each fragment, the ratio of the signals from the two detectors, and the 3′ terminal base deduced from the ratio. The distribution of fragments and the identities of the 3′ terminal base are as predicted from the known sequence of phage λ DNA.

TABLE II

| Fragment size, in nucleotides | Ratio of detector signals T channel: R channel | Deduced 3′ terminal base |
|---|---|---|
| 34 | 2.73 | G |
| 35 | 2.85 | G |
| 36 | 2.18 | A |
| 37 | 0.61 | T |
| 66 | 2.14 | A |
| 67 | 2.81 | G |
| 68 | 1.50 | C |
| 69 | 2.21 | A |
| 84 | 0.76 | T |
| 85 | 2.81 | G |
| 86 | 2.86 | G |

TABLE II-continued

| Fragment size, in nucleotides | Ratio of detector signals T channel: R channel | Deduced 3' terminal base |
|---|---|---|
| 87 | 2.28 | A |
| 118 | 2.19 | A |
| 119 | 0.63 | T |
| 120 | 1.48 | C |
| 121 | 0.69 | T |
| 136 | 2.15 | A |
| 137 | 2.81 | G |
| 138 | 0.86 | T |
| 139 | 2.82 | G |
| 164 | 2.19 | A |
| 165 | 2.81 | G |
| 166 | 2.28 | A |
| 167 | 1.83 | G |
| 185 | 1.45 | C |
| 186 | 2.82 | G |
| 187 | 2.86 | G |
| 188 | 2.91 | G |
| 223 | 2.19 | A |
| 224 | 2.26 | A |
| 225 | 2.16 | A |
| 226 | 0.80 | T |
| 240 | 1.38 | C |
| 241 | 2.22 | A |
| 242 | 2.19 | A |
| 243 | 1.41 | C |
| 269 | 2.23 | A |
| 270 | 1.30 | C |
| 271 | 2.25 | A |
| 272 | 1.63 | C |

EXAMPLE 12

LABELING OF BLUNT-END FRAGMENTS—CHARACTERIZATION OF PHAGE λ DNA USING BSTEII AS THE PRIMARY CLEAVAGE ENZYME AND ALUI AS THE SECONDARY CLEAVAGE ENZYME

A quantity of 10 μg phage λ DNA digested with the restriction enzyme BstEII (New England BioLabs; 0.4 μg/mL) was dispensed into a 1.5 mL Eppendorf tube, then the following additions were made: 10 μL 10X Klenow buffer (0.5M NaCl; 0.1M Tris-HCl, pH 7.5; 0.1M MgCl$_2$; 0.01M dithiothreitol), 54 μL H$_2$O, 5 μL 0.4 mM biotin-11-dUTP (Bethesda Research Laboratories), 5 μL of a solution containing 1 mM dATP, 1 mM dCTP, and 1 mM dGTP, and 1 μL of a solution containing the large fragment (Klenow fragment) of DNA polymerase I (Bethesda Research Laboratories; 6 units/μL). This reaction was incubated at 20° C. for 30 minutes. The DNA was precipitated by adding 100 μL 5M ammonium acetate plus 500 μL ethanol, mixing, and storing at −20° C. The DNA was recovered by centrifuging at 14,000 rpm for 15 minutes. After discarding the supernatant, the DNA pellet was dried under vacuum for 10 minutes, and dissolved in 85 μL TE (10 mM Tris-HCl, pH 7.4; 1 mM EDTA). Secondary cleavage with AluI was accomplished by adding 10 μL 10X AluI reaction buffer (0.5M NaCl; 0.06M Tris-HCl, pH 7.6; 0.06M MgCl$_2$; 0.06M 2-mercaptoethanol; 1 mg/ml bovine serum albumin), and 5 μL restriction enzyme AluI (New England BioLabs; 5 units/μL). The reaction was incubated at 37° C. for 3 hours. The DNA was precipitated by adding 100 μL 5M ammonium acetate plus 500 μL ethanol, mixing, and storing at −20° C. The DNA was recovered by centrifuging at 14,000 rpm for 15 minutes. After discarding the supernatant, the DNA pellet was dried under vacuum for 10 minutes, dissolved in 100 μL TE (10 mM Tris-HCl, pH 7.4; 1 mM EDTA), and stored at 4° C. This provides a stock solution at a DNA concentration of 0.1 μg/μL that will be referred to as phage λ BstEII-biotin-AluI.

One μg of the phage λ BstEII-biotin-AluI DNA was incubated with 10 μg streptavidin-CrO$_2$ particles and washed two times with 100 μL 100 mM NaCl; 10 mM Tris-HCl, pH 7.4; 1 mM EDTA: 100 ]ag/ml bovine serum albumin as described in Example 11. In order to label the DNA fragments with the fluorescent reporters, the particles were suspended in 11 μL TE and the following additions were made: 4 μL 5X Sequenase buffer (0.2M Tris-HCl, pH 7.5; 0.05M MgCl$_2$; 0.25M NaCl), 4 μL of a solution containing 100 μM 7-(SF505-Sar-AP3)ddC$^7$GTP; 100 μM 7-(SF512-Sar-AP3)ddC$^7$ATP; 100 μM 5-(SF519-Sar-AP3)ddCTP; and 100 μM 5-(SF526-Sar-AP3)ddTTP, and 1 μL (2 units) Sequenase (modified T7 DNA polymerase from U.S. Biochemical Corp.). The reaction was incubated at 37° C. for 1 hour. The sample tube was placed in the magnetic rack to immobilize the particles and the supernatant was discarded. As described in Example 11, the particles were washed three times with 100 μL 0.17% (w/v) Triton X-100; 100 mM NaCl; 10 mM Tris-HCl, pH 7.4; 1 mM EDTA and the labeled fragments were eluted in 5 μL 95% (v/v) formamide; 12.5 mM EDTA. The electrophoresis and detection conditions outlined in Example 10 were used to analyze the size and reporter identity for the labeled fragments. Table III presents the fluorescent fragments detected in the size range of 50–320 nucleotides. Based on the known sequence of phage λ DNA, the following labeled fragments are expected:

| 53 | 93 | 185 | 245 |
| 68 | 94 | 197 | 251 |
| 70 | 103 | 211 | 274 |
| 75 | 177 | 243 | 318 |

Each of these labeled fragments is observed and the reporter identity indicates that the terminal base in each case is a G. This is expected because cleavage of DNA with AluI generates the following blunt end:

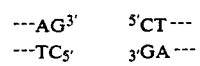

Thus, the 3' exonuclease activity of the T7 DNA polymerase removes the 3' terminal G and replaces it with 7-(SF505-Sar-AP3)ddC$^7$G. Other fragments besides the expected G-labeled fragments are observed. This indicates that, in some cases, the 3' exonuclease activity removes more than just the 3'-terminal G before adding a fluorescently tagged dideoxynucleotide. Overall, though, this experiment demonstrates that blunt-end fragments can be labeled with nucleotide-specific reporters. Although more complex than expected, the distribution of labeled fragments makes a distinctive pattern that is characteristic of the DNA sample. Thus, this characteristic pattern can still be used as a fingerprint to identify a particular DNA segment and differentiate it from other segments.

TABLE III

| Fragment size, in nucleotides | Ratio of detector signals T channel: R channel | Deduced 3' terminal base |
|---|---|---|
| 51 | 3.13 | G |
| 52 | 2.48 | A |

TABLE III-continued

| Fragment size, in nucleotides | Ratio of detector signals T channel: R channel | Deduced 3' terminal base |
|---|---|---|
| 53 | 3.12 | G |
| 66 | 3.30 | G |
| 68 | 3.10 | G |
| 70 | 3.12 | G |
| 73 | 3.11 | G |
| 75 | 3.09 | G |
| 81 | 3.15 | G |
| 93 | 3.11 | G |
| 94 | 3.10 | G |
| 102 | 2.51 | A |
| 103 | 3.09 | G |
| 107 | 3.13 | G |
| 137 | 3.10 | G |
| 163 | 3.12 | G |
| 167 | 3.10 | G |
| 170 | 3.10 | G |
| 172 | 3.10 | G |
| 175 | 2.52 | A |
| 176 | 2.49 | A |
| 177 | 3.09 | G |
| 183 | 3.10 | G |
| 184 | 2.50 | A |
| 185 | 3.10 | G |
| 193 | 3.15 | G |
| 195 | 2.50 | A |
| 196 | 2.46 | A |
| 197 | 3.10 | G |
| 199 | 3.09 | G |
| 211 | 3.11 | G |
| 222 | 3.14 | G |
| 243 | 3.03 | G |
| 245 | 3.03 | G |
| 247 | 3.07 | G |
| 250 | 2.44 | A |
| 251 | 3.01 | G |
| 259 | 3.02 | G |
| 267 | 2.98 | G |
| 270 | 3.04 | G |
| 272 | 2.41 | A |
| 273 | 2.38 | A |
| 274 | 3.02 | G |
| 309 | 3.03 | G |
| 312 | 3.12 | G |
| 314 | 3.03 | G |
| 315 | 3.05 | G |
| 317 | 2.40 | A |
| 318 | 3.01 | G |

EXAMPLE 13

LABELING OF FRAGMENTS WITH 3' OVERHANGS—CHARACTERIZATION OF PHAGE λ DNA USING BSTEII AS THE PRIMARY CLEAVAGE ENZYME AND HPHI AS THE SECONDARY CLEAVAGE ENZYME

Following the procedure in Example 12, 10 μg phage λ DNA digested with Bst EII was treated with biotin-11-dUTP, dATP, dCTP, dGTP, and Klenow fragment, precipitated, and dissolved in 100 μL TE (10 mM Tris-HCl, pH 7.4; 1 mM EDTA). This sample was passed through a G-50 Select-D spin column (5 Prime-3 Prime, Inc.; Paoli, Pa.) and the excluded volume (122 μL) was incubated at 70° C. for 10 minutes. Secondary cleavage with HphI was accomplished by adding 20 μL 10X HphI reaction buffer (0.06M KCl; 0.1M Tris-HCl, pH 7.4; 0.1M MgCl$_2$; 0.01M dithiothreitol; 2 mg/ml bovine serum albumin), 38 μL H$_2$O, and 20 μL restriction enzyme HphI (New England BioLabs; 4 units/μL). The reaction was incubated at 37° C. for 2 hours. The DNA was precipitated by adding 200 μL 5M ammonium acetate plus 1 mL ethanol, mixing, and storing at −20° C. The DNA was recovered by centrifuging at 14,000 rpm for 15 minutes. After discarding the supernatant, the DNA pellet was dried under vacuum for 10 minutes, dissolved in 100 μL TE, and stored at 4° C. This provides a stock solution at a DNA concentration of 0.1 μg/μL that will be referred to as phage λ BstEII-biotin-HphI.

Following the procedure in Example 12, 1 μg phage λ BstEII-biotin-HphI DNA was attached to 10 μg CrO$_2$-streptavidin particles, washed two times, labeled with fluorescently tagged dideoxynucleotides, washed three times, eluted, and subjected to electrophoresis and fluorescence detection. Table IV presents the fluorescent fragments detected in the size range of 30–230 nucleotides. Based on the known sequence of phage λ DNA, the following labeled fragments are expected:

| 36 | 112 | 122 | 196 |
| 59 | 113 | 145 | 224 |
| 84 | 117 | 166 | |
| 95 | 120 | 177 | |

Most of these labeled fragments are observed, but quite a few other labeled fragments are also observed. This indicates that the 3' exonuclease of T7 DNA polymerase is more active than expected on the HphI ends, just as it was on the AluI ends in Example 12. Thus, for each available HphI end, a few labeled fragments are observed rather than just one. Still, the main point is that DNA fragments with 3' overhangs can be labeled with nucleotide-specific reporters. Again, a characteristic pattern is generated that serves as a fingerprint to identify the DNA sample.

TABLE IV

| Fragment size, in nucleotides | Ratio of detector signals T channel: R channel | Deduced 3' terminal base |
|---|---|---|
| 29 | 2.97 | G |
| 31 | 3.05 | G |
| 34 | 1.67 | C |
| 35 | 1.73 | C |
| 36 | 1.71 | C |
| 54 | 2.98 | G |
| 55 | 2.47 | A |
| 57 | 3.03 | G |
| 59 | 1.98 | C |
| 84 | 3.01 | G |
| 85 | 1.94 | C |
| 87 | 3.09 | G |
| 89 | 2.62 | A |
| 105 | 3.05 | G |
| 109 | 2.69 | A |
| 112 | 3.09 | G |
| 114 | 3.25 | G |
| 115 | 2.25 | A |
| 117 | 2.36 | A |
| 118 | 2.39 | A |
| 119 | 1.27 | T |
| 120 | 2.33 | A |
| 121 | 2.44 | A |
| 122 | 3.03 | G |
| 137 | 2.98 | G |
| 138 | 3.07 | G |
| 139 | 2.41 | A |
| 141 | 3.08 | G |
| 143 | 1.85 | C |
| 144 | 1.78 | C |
| 164 | 3.03 | G |
| 165 | 2.43 | A |
| 166 | 3.03 | G |
| 175 | 2.49 | A |
| 176 | 3.03 | G |
| 177 | 2.43 | A |
| 178 | 2.43 | A |
| 190 | 3.02 | G |

TABLE IV-continued

| Fragment size, in nucleotides | Ratio of detector signals T channel: R channel | Deduced 3' terminal base |
|---|---|---|
| 193 | 2.98 | G |
| 195 | 2.42 | A |
| 196 | 2.37 | A |
| 217 | 3.01 | G |
| 222 | 2.92 | G |
| 224 | 1.82 | C |

EXAMPLE 14

COMPARISON OF THE DNA OF TWO STRAINS OF PSEUDORABIES VIRUS

Following the procedure of Denniston et al. (Gene 15:365-378, 1981), DNA was prepared from the Bartha strain and the Becker strain of pseudorabies virus, a herpes virus that infects pigs. Each type of DNA was digested with the restriction enzyme SalI by incubating 5 $\mu$g DNA in a 200-$\mu$L reaction mixture containing 150 mM NaCl, 10 mM Tris-HCl, pH 8.0, 10 mM MgCl$_2$, 10 mM $\beta$-mercaptoethanol, 100 $\mu$g/mL bovine serum albumin, and 160 units SalI (New England BioLabs). Each reaction was incubated at 37° C. for 2 hours. Each DNA sample was precipitated by adding 200 $\mu$L 5M ammonium acetate plus 1 mL ethanol, mixing, and placing on dry ice for 20 minutes. The DNA was recovered by centrifuging at 14,000 rpm for 15 minutes. After discarding the supernatant, each DNA pellet was dried under vacuum for 10 minutes, then dissolved in 79 $\mu$L TE (10 mM Tris-HCl, pH 7.4; 1 mM EDTA). In order to attach biotin at the SalI ends, the following additions were made to each sample: 10 $\mu$L 10X Klenow buffer (0.5M NaCl; 0.1M Tris-HCl, pH 7.5; 0.1M MgCl$_2$; 0.01M dithiothreitol), 5 $\mu$L 0.4 mM biotin-11-dUTP (Bethesda Research Laboratories), 5 $\mu$L of a solution containing 1 mM dATP, 1 mM dCTP, and 1 mM dGTP, and 1 $\mu$L of a solution containing the large fragment (Klenow fragment) of DNA polymerase I (Bethesda Research Laboratories; 6 units/$\mu$L). Each reaction was incubated at 20° C. for 30 minutes. Each DNA sample was precipitated by adding 100 $\mu$L 5M ammonium acetate plus 500 $\mu$L ethanol, mixing, and storing at −20° C. The DNA was recovered by centrifuging at 14,000 rpm for 15 minutes. After discarding the supernatant, each DNA pellet was dried under vacuum for 10 minutes, dissolved in 100 $\mu$L TE (10 mM Tris-HCl, pH 7.4; 1 mM EDTA), and passed through a G-50 Select-D spin column (5 Prime-3 Prime, Inc.; Paoli, Pa.). Each excluded volume (approx. 125 $\mu$L) was incubated at 70° C. for 10 minutes, then stored at 4° C. Secondary cleavage with FokI was accomplished by adding the following to each DNA sample: 20 $\mu$L 10X FokI reaction buffer (0.2M KCl; 0.1M Tris-HCl, pH 7.5; 0.1M MgCl$_2$; 0.06M 2-mercaptoethanol; 1 mg/ml bovine serum albumin), 35 $\mu$L H$_2$O, and 20 $\mu$L restriction enzyme FokI (New England BioLabs; 3 units/$\mu$L). Each reaction was incubated at 37° C. for 3 hours. Each DNA sample was precipitated by adding 200 $\mu$L 5M ammonium acetate plus 1 mL ethanol, mixing, and storing at −20° C. The DNA was recovered by centrifuging at 14,000 rpm for 15 minutes. After discarding the supernatant, each DNA pellet was dried under vacuum for 10 minutes, dissolved in 50 $\mu$L TE (10 mM Tris-HCl, pH 7.4; 1 mM EDTA), and stored at 4° C. This provides stock solutions each at a DNA concentration of 0.1 $\mu$g/$\mu$L that will be referred to as Bartha SalI-biotin-FokI and Becker SalI-biotin-FokI.

Figure 2:
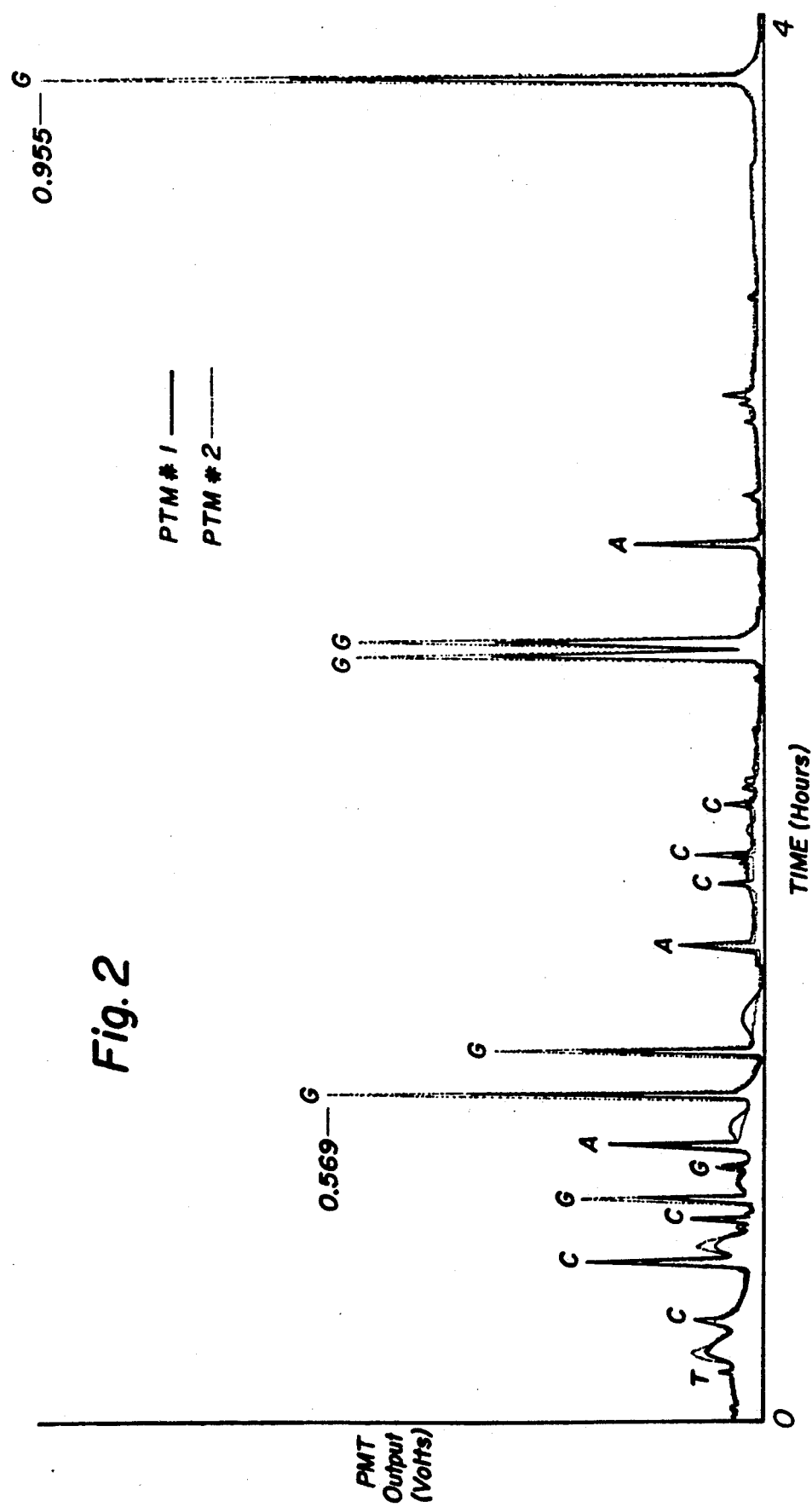
FIG. 2 is a plot of photomultiplier tube output as the ordinant and time as the abscissa depicting fluorescently labeled DNA fragments from the Bartha strain of pseudorabies virus.

Following the procedure in Example 11, 1 $\mu$g samples of Bartha SalI-biotin-FokI DNA and Becker SalI-biotin-FokI DNA were attached to 10 $\mu$g CrO$_2$-streptavidin particles and washed two times. In order to label the DNA fragments with the fluorescent reporters, each sample of particles were suspended in 11 $\mu$L TE and the following additions were made: 4 $\mu$L 5X reverse transcriptase buffer (250 mM Tris-HCl, pH 8.3 at 42° C.; 40 mM MgCl$_2$; 150 mM KCl; 5 mM dithiothreitol), 4 $\mu$L of a solution containing 100 $\mu$M 7-(SF505-Sar-AP3)ddC$^7$GTP; 100 $\mu$M 7-(SF512-Sar-AP3)ddC$^7$ATP; 100 $\mu$M 5-(SF519-Sar-AP3)ddCTP; and 100 $\mu$M 5-(SF526-Sar-AP3)ddTTP, and 1 $\mu$L (3 units) reverse transcriptase (New England Nuclear). Each reaction was incubated at 42° C. for 1 hour. By using this labeling protocol that contains no deoxynucleotides, only the first position in each FokI four-base overhang is labeled. This means that each labeled FokI end generates a single peak rather than the quartet of peaks observed in Examples 10 and 11. Following the procedure in Example 11, each sample of particles was washed three times, and the labeled fragments were eluted, then subjected to electrophoresis and fluorescence detection. Fluorescent fragments detected in the size range 50-240 nucleotides are shown in FIG. 1 for the Becker sample and in FIG. 2 for the Bartha sample. Comparison of these two figures shows that the two strains have 15 fragments in common. These common fragments have the same size as indicated by mobility time and the same terminal base as indicated by reporter identity. The Bartha sample has 2 fragments not present in the Becker sample. The Becker sample has 3 fragments not present in the Bartha sample. These results show that the Bartha and Becker strains of pseudorabies are very similar but not identical. This comparison demonstrates how the fingerprinting procedure can be used to compare DNA samples for similarity.

We claim:

1. A method for mapping a DNA segment made up of duplex strands of nucleotides by
    cleaving the segment with a first restriction enzyme to produce fragments of DNA, each having a cleaved end,
    attaching a reporter specific to a cleaved end nucleotide in each fragment,
    cleaving the DNA fragments with a second restriction enzyme to produce short fragments,
    separating the short fragments according to size, and
    analyzing the short, separated fragments for the presence of reporters, the size and reporter identity being indicative of the character of each DNA fragment.

2. The method as set forth in claim 1 wherein the segment cleaving produces fragments of DNA with each cleaved end having one strand with a residue of nucleotides and a corresponding recessed strand and includes the step of attaching a reporter labeled nucleotide to the recessed strand to form a base pair with at least one residue nucleotide, the reporter being specific to each type of nucleotide.

3. The method as set forth in claim 2 wherein a third enzyme is used in conjunction with and in addition to the first enzyme or second enzyme to cleave different length fragments.

4. The method as set forth in claim 1 wherein a third enzyme is used in conjunction with and in addition to the first enzyme or second enzyme to cleave different length DNA fragments.

5. The method as set forth in claim 3 wherein the analysis is accomplished in real time.

6. The method of claim 2 wherein the segment cleaving step produces DNA fragments having a 5' overhang residue of nucleotides.

7. The method of claim 2 wherein the segment cleaving step produces DNA fragments having a 3' overhang residue of nucleotides.

8. The method of claim 7 wherein the reporter attachment is accomplished by using a polymerase exhibiting 3' exonuclease activity.

9. The method of claim 8 wherein the polymerase is selected from the group consisting of DNA polymerase I, T7 DNA polymerase, and T4 DNA polymerase.

10. The method of claim 2 wherein the segment cleaving step produces DNA fragments having blunt ends.

11. A method of mapping DNA segments made up of duplex strands of nucleotides using a reporter comprising:

reacting a mixture of DNA segments and a first restriction enzyme that cleaves the DNA to provide DNA fragments each with 5' or 3' overhang strands and a corresponding 3' or 5' recessed strand or with blunt ends, incubating the DNA fragments with a DNA polymerase and a mixture of unlabeled deoxynucleotides and specific reporter labeled dideoxynucleotides to add nucleotides to the recessed strands complementary to the nucleotides in the overhang strands, reacting the incubated DNA fragments with a second restriction enzyme to produce short DNA fragments some of which include the reporter labeled dideoxynucleotides and hence are reporter labeled, separating the short DNA fragments according to size, and detecting a reporter for each labeled fragment thereby identifying the 3' terminal added dideoxynucleotides.

12. The method as set forth in claim 11 which includes the step of:

correlating the size and reporter identification of each labeled short DNA fragment of the DNA segment.

13. The method as set forth in claim 12 wherein the ratio of labeled dideoxynucleotides to unlabeled deoxynucleotides is varied inversely according to the number of nucleotides in the overhang strands.

14. The method as set forth in claim 11 wherein a third enzyme is used in conjunction with and in addition to the first enzyme or second enzyme to cleave the DNA segments into different length fragments.

15. The method as set forth in claim 11 wherein the DNA fragments are reacted only with reporter labeled dideoxynucleotides.

16. The method as set forth in claim 11 wherein the first restriction enzyme is an ambiguous-end restriction enzyme.

17. The method as set forth in claim 13 wherein the first restriction enzyme is an ambiguous-end restriction enzyme.

18. The method set forth in claim 11 wherein the first restriction enzyme is an exact-end restriction enzyme.

19. The method set forth in claim 13 wherein the first restriction enzyme is an exact-end restriction enzyme.

20. The method as set forth in claim 11 wherein the ratio of labeled dideoxynucleotides to unlabeled deoxynucleotides is varied inversely according to the number of nucleotides in the overhang strands.

21. The method as set forth in claim 13 wherein a third enzyme is used in conjunction with and in addition to the first enzyme or second enzyme to cleave the DNA segments into different length fragments.

22. The method as set forth in claim 13 wherein the DNA fragments are reacted only with reporter labeled dideoxynucleotides.

23. The method as set forth in claim 13 wherein the first restriction enzyme is an ambiguous-end restriction enzyme.

24. A method for mapping DNA segments made up of duplex strands of nucleotides using specific binding pairs, one member of the pair being immobilized on a solid support, by the steps of:

(a) cleaving each segment with a first restriction enzyme to produce fragments of DNA each having a cleaved end, (b) derivatizing cleaved end nucleotides in each fragment with the other member of the specific binding pair, (c) cleaving the derivatized DNA fragments with a second restriction enzyme to produce short DNA fragments, (d) binding the short fragments to the immobilized member, leaving a free end nucleotide on each derivatized fragment, (e) separating the derivatized fragments from the non-derivatized fragments, (f) attaching a reporter to one of the free end nucleotides in each derivatized shorter fragment, (g) separating the reporter labeled, separated fragments from the solid support, and (h) fractionating the reporter labeled fragments according to size.

25. The method set forth in claim 24 which includes the step of: analyzing the fractionated fragments for the presence of labeled fragments as a function of size.

26. The method of claim 25 wherein the reporter is nucleotide specific.

27. The method of claim 24 wherein the reporter is nucleotide specific.

28. The method of claim 27 wherein the solid support is beads that are water insoluble and stable to the physical and chemical conditions of steps d, e, f and g of claim 24.

29. The method of claim 28 wherein the beads are chromium dioxide.

30. The method of claim 29 wherein the beads are separated from their surrounding environment by a magnetic field.

31. The method of claim 26 wherein the solid support is beads that are water insoluble and stable to the physical and chemical conditions of steps d, e, f and g of claim 24.

32. The method of claim 31 wherein the beads are chromium dioxide.

33. The method of claim 28 wherein the step of subjecting the short fragments to the immobilized member to attach the derivatized short fragments to the beads includes the step of separating the beads with attached derivatized short fragments from the non-derivatized fragments.

34. The method of claim 33 wherein the beads are chromium dioxide.

35. The method of claim 34 wherein the step of separating the beads is accomplished by the use of a magnetic field.

36. The method of claim 24 wherein the free end nucleotide is on the 3' strand of DNA.

37. A method for mapping DNA segments made up of duplex strands of nucleotides using specific binding substances (one and the other), one substance being immobilized on a solid support, by the steps of:

cleaving each segment with a first restriction enzyme to produce fragments of DNA each having a cleaved end, attaching the other substance to the cleaved ends to provide anchor ends, cleaving the DNA fragments with a second restriction enzyme to provide shorter DNA fragments and free ends, separating shorter fragments with an anchor end from the remaining shorter fragments by binding the anchor ends to the one substance, attaching reporter labeled nucleotides to the free end of each separated shorter fragment, removing the separated shorter fragments from the one substance, fractionating the removed shorter fragments.

38. A method for mapping DNA segments made up of duplex strands of nucleotides using specific binding pairs, one member of the pair being immobilized on a solid support, by the steps of:

(a) cleaving each segment with a first restriction enzyme to produce fragments of DNA each having a cleaved end, (b) derivatizing cleaved end nucleotides in each fragment with the other member of the specific binding pair, (c) cleaving the derivatized DNA fragments with a second restriction enzyme to produce short DNA fragments, the second cleaved ends being non-derivatized, (d) attaching a reporter to each of the non-derivatized ends of the short fragments, (e) binding the short fragments with derivatized ends to the one member, (f) separating the bound, derivatized fragments, some of which are reporter-labeled at one end, from the fragments that are not derivatized at either end, (g) separating the bound, reporter-labeled fragments from the solid support, (h) fractionating the reporter labeled fragments according to size.

39. A method for mapping DNA segments made up of duplex strands of nucleotides using specific binding pairs, one member of the pair being immobilized on a solid support, by the steps of:

(a) cleaving each segment with a first restriction enzyme to produce fragments of DNA each having a cleaved end, (b) derivatizing cleaved end nucleotides in each fragment with the other member of the specific binding pair, (c) cleaving the derivatized DNA fragments with a second restriction enzyme to produce short DNA fragments, binding the derivatized fragments to the one member, (d) cleaving the bound DNA fragments with a second restriction enzyme to produce short DNA fragments, some of which have one bound, derivatized and one free end and some of which are not derivatized at either end, (e) separating the bound short fragments from the unbound short fragments, (f) attaching a reporter to one of the free end nucleotides in each bound short fragment, (g) separating the reporter-labeled, bound fragments from the solid support, (h) fractionating the reporter labeled fragments according to size.

* * * * *